United States Patent [19]
Kim

[11] Patent Number: 5,945,125
[45] Date of Patent: *Aug. 31, 1999

[54] CONTROLLED RELEASE TABLET

[75] Inventor: Cherng-ju Kim, Lansdale, Pa.

[73] Assignee: Temple University, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/667,238

[22] Filed: Jun. 21, 1996

Related U.S. Application Data

[63] Continuation-in-part of application No. 08/395,792, Feb. 28, 1995, abandoned.

[51] Int. Cl.$^6$ ............................................. A61K 9/24
[52] U.S. Cl. ..................................... 424/473; 424/468
[58] Field of Search ........................ 424/473, 468

[56] References Cited

U.S. PATENT DOCUMENTS

| | | | |
|---|---|---|---|
| 3,113,076 | 12/1963 | Jacobs | 424/467 |
| 3,641,237 | 2/1972 | Gould et al. | 424/427 |
| 3,946,106 | 3/1976 | Chien et al. | 424/425 |
| 4,053,580 | 10/1977 | Chien et al. | 424/425 |
| 4,217,898 | 8/1980 | Theeuwes | 424/433 |
| 4,235,236 | 11/1980 | Theeuwes | 604/892.1 |
| 4,309,996 | 1/1982 | Theeuwes | 604/892.1 |
| 4,320,759 | 3/1982 | Theeuwes | 604/892.1 |
| 4,610,870 | 9/1986 | Jain et al. | 424/465 |
| 4,624,848 | 11/1986 | Lee | 424/486 |
| 4,749,576 | 6/1988 | Lee | 424/486 |
| 4,756,911 | 7/1988 | Drost et al. | 424/486 |
| 4,784,858 | 11/1988 | Ventouras | 424/468 |
| 4,792,452 | 12/1988 | Howard et al. | 424/475 |
| 4,803,081 | 2/1989 | Falk et al. | 424/488 |
| 4,816,262 | 3/1989 | McMullen | 424/467 |
| 4,837,111 | 6/1989 | Deters | 424/473 |
| 4,844,910 | 7/1989 | Leslie et al. | 424/494 |
| 4,891,223 | 1/1990 | Ambegaonkar et al. | 424/408 |
| 4,942,040 | 7/1990 | Ragnarsson et al. | 424/486 |
| 5,051,263 | 9/1991 | Barry et al. | 424/490 |
| 5,128,143 | 7/1992 | Baichwal et al. | 424/464 |
| 5,132,116 | 7/1992 | Sournac et al. | 424/469 |
| 5,252,338 | 10/1993 | Jao et al. | . |
| 5,273,758 | 12/1993 | Royce | 424/465 |
| 5,273,760 | 12/1993 | Oshlack et al. | 424/480 |
| 5,393,765 | 2/1995 | Infeld et al. | 514/365 |
| 5,395,626 | 3/1995 | Kotwal et al. | 424/472 |

FOREIGN PATENT DOCUMENTS

| | | |
|---|---|---|
| 231826A2 | 8/1987 | European Pat. Off. . |
| 665045A1 | 7/1995 | European Pat. Off. . |

OTHER PUBLICATIONS

A. G. Hanson, A. Giardino, J. R. Cardinal, and W. Curatolo. "Perforated Coated Tablets for Controlled Release of Drugs at a Constant Rate," *Journal of Pharmaceutical Sciences*, vol. 77, No. 4, Apr. 1988, pp. 322–324.

P. J. Sheskey, T. D. Cabelka, R. T. Robb, and B. M. Boyce. "Use of Roller Compaction in the Preparation of Controlled-Release Hydrophilic Matrix Tablets Containing Methylcellulose and Hydroxypropyl Methylcellulose Polymers," *Pharmaceutical Technology*, Sep. 1994, pp. 133–150.

(List continued on next page.)

*Primary Examiner*—D. Gabrielle Brouillette
*Attorney, Agent, or Firm*—Ratner & Prestia

[57] ABSTRACT

A controlled release tablet including a pharmaceutical agent and an excipient. The excipient includes at least about 60% of a water swellable polymer and a lubricant. The water swellable polymer is chosen such that the swelling rate of the polymer is equal to the dissolution rate of the swollen polymer. The excipient may also include such other ingredients as diluents, fillers, binders, solubilizers, emulsifiers, and other pharmacologically inactive compounds. The polymer is chosen with the pharmaceutical agent in mind such that the tablet will be fully dissolved at the same time that the last of the pharmaceutical agent is released.

25 Claims, 31 Drawing Sheets

OTHER PUBLICATIONS

J. L. Ford, M. H. Rubenstein, and J. E. Hogan. Formulation of Sustained Release Promethazine Hydrochloride Tablets Using Hydroxypropylmethylcellulose Matrices, *International Journal of Pharmaceutics*, 24 (1985), pp. 327–338.

J. L. Ford, M. H. Rubenstein, and J. E. Hogan, "Propranolol Hydrochloride and Aminophylline Release from Matrix Tablets Containing Hydroxypropylmethylcellulose," *International Journal of Pharmaceutics*, 24 (1985), pp. 339–350.

L. W. S. Cheong, P. W. S. Heng, and L. F. Wong. Relationship Between Polymer Viscosity and Drug Release from a Matrix System, *Pharmaceutical Research*, vol. 9, No. 11, 1992, pp. 1510–1514.

J. L. Ford, M. H. Rubenstein, F. McCaul, J. E. Hogan, and P. J. Edgar. "Importance of Drug Type, Tablet Shape and Added Diluents of Drug Release Kinetics for Hydroxypropylmethylcellulose Matrix Tablets," *International Journal of Pharmaceutics*, 40 (1987), pp. 223–234.

Advance ACS Abstracts, vol. 3, No. 3, Feb. 1, 1995, p. 107.

CONTROLLED RELEASE TABLET

CROSS REFERENCE TO RELATED APPLICATIONS

This application is a continuation-in-part of U.S. patent application Ser. No. 08/395,792, filed Feb. 28, 1995, now abandoned.

BACKGROUND OF THE INVENTION

1. Field of the Invention

The present invention relates to sustained release tablets including any of a wide array of pharmaceutical products and an excipient.

2. Description of the Related Art

Many attempts have been made in the pharmaceutical art to provide a composition which would enable the production of sustained release tablets. These attempts have produced compositions which are able to release pharmaceutical agents over a long period of time. However, such release has not been constant. Rather, prior art sustained release compositions generally release a disproportionate amount of their pharmaceutical agent quickly after ingestion by a patient. This results in a quick spike in the level of medication in the patient's bloodstream. Such a delivery method may be desirable where the pharmaceutical is intended to alleviate particular symptoms of a patient. However, there are many instances where a spike in the medication level in a patient is undesirable, as where pharmaceuticals are used to treat a chronic condition. Further, extended release of biologically active drugs is highly desirable for drugs that have characteristically short half lives.

Monolithic systems, composed of hydrophobic polymers and other excipients, are commonly used for extended release dosage forms because they are not costly or difficult to produce. However, such systems often provide a square-root-of-time (sqrt) kinetics (i.e. the amount of pharmaceutical agent released is proportional to the square root of the time since the drug was ingested). There are several ways to improve the release kinetics of extended release dosage forms. Incorporation of hydrophilic polymers into monolithic matrices modifies square root kinetics due to the swelling of the polymer. In particular, monolithic matrix systems controlled by the swelling/erosion processes of hydrophilic polymers can improve the pharmaceutical agent kinetics. However, even in these systems, the release rate of the pharmaceutical agent generally varies significantly with time.

Hydrophilic polymers alone have also been investigated for controlled drug release. The hydrophilic polymers such as hydroxypropylmethyl cellulose (HPMC) and polyvinylalcohol (PVA), which form gels upon contact with water and erode slowly, have been utilized for oral drug delivery systems. Cross-linked poly(ethylene oxide) has also been investigated for controlled drug delivery. However, attempts to use these materials to produce a constant, controlled, sustained drug release have thus far proven ineffective.

SUMMARY OF THE INVENTION

The present invention provides a controlled release tablet including a pharmaceutical agent and an excipient. The excipient includes at least about 50% of a water swellable polymer and a lubricant. The water swellable polymer is chosen such that the swelling rate of the polymer is equal to the dissolution rate of the swollen polymer. The lubricant is generally present in an amount of up to 3% of the excipient as a whole. The excipient may also include such other ingredients as diluents, fillers, binders and other pharmacologically inactive compounds. Further, the polymer and pharmaceutical agent are complementary. In selecting a water swellable polymer, the polymer should be chosen with the pharmaceutical agent in mind such that the tablet will be fully dissolved at the same time that the last of the pharmaceutical agent is released.

The preferred water swellable polymer is polyethylene oxide. The pharmaceutical agent is released from the tablet at a rate which can be expressed by $M_t/M_T = kt^n$ where t is time, $M_t$ is the amount of the pharmaceutical agent which has been released at time t, $M_T$ is the total amount of the pharmaceutical agent contained in the tablet, k is a constant, and n is the release kinetics exponent and has a value between about 0.89 and 1.0.

DETAILED DESCRIPTION OF THE PREFERRED EMBODIMENTS

Figure 1:
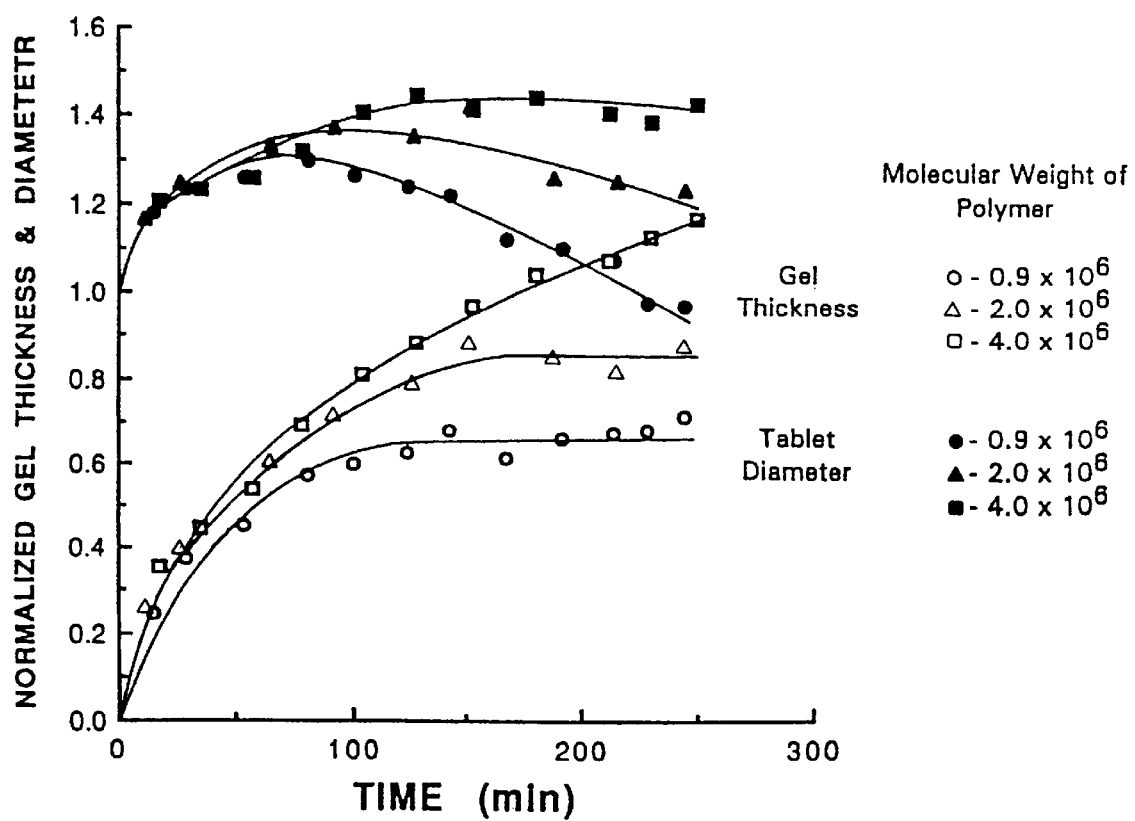
FIG. 1 is a graph of the gel thickness and tablet diameter versus time for various molecular weights of PEO polymer.

The excipients of the present invention have been formulated to allow controlled sustained release of any one of a number of pharmaceutical agents. The excipients of the present invention generally comprise a hydrophilic polymer and a lubricant. Other pharmacologically inactive materials also can be added. The excipients can be mixed with a wide range of medications and directly compressed into solid dosage tablets.

The following drugs with which the present invention may be used are set forth as examples only. Any suitable drug may be used with the present invention, including nifedipine, diclofenac sodium, salicylic acid, theophylline anhydrous, sulfapyridine, sulfadrazine, propranolol hydrochloride, glipizide, and diltiazem hydrochloride. Polyethylene glycol is generally used to increase the solubility of relatively insoluble drugs to encourage absorption by the body. Other solubilizers as described below may be used. The polymers set forth herein may be compressed into tablets directly. Optionally, binders, fillers, or other typical compounding agents may be added to adjust the properties of the final tablets. Particularly, but without limitation, the following compounds may be included: lactose, dextrose, sucrose, and calcium phosphate.

In addition, sulphathiazole may be used as the drug with the present invention. The above-listed drugs, optionally, may be granulated into fine particles and dissolved in a solvent such as ethanol which will not dissolve the polymeric material being used.

Specifically, the polymeric materials useful in the present invention will depend to a certain extent on the pharmaceutical agent chosen to be administered. Polymers of choice include uncrosslinked poly(ethylene oxide) (PEO) and hydroxypropylmethylcellulose (HPMC) both of varying molecular weight and viscosity, respectively. HPMC is available on the basis of viscosity measured in a 2% solution in water. PEO is available on the basis of molecular weight. Both PEO and HPMC are useful alone. Alternatively, mixtures of the two materials, or mixtures of various viscosities or molecular weights of either compound may be used in the present invention.

During the release of drugs from hydrophilic matrices of PEO or HPMC, two mechanistic phenomena take place: the swelling and the erosion of the polymer. The release kinetics of the drug from the tablet are dependent upon the relative magnitude of the rate of polymer swelling at the moving rubbery/glassy front and the rate of polymer erosion at the swollen polymer/dissolution medium front. It is most preferable to attain the synchronization of the velocities of the swelling front and the erosion front in order to achieve zero-order release kinetics from hydrophilic polymer matrices.

The release kinetics for the release of a pharmaceutical agent from a tablet can be approximated by the following equation:

$$M_t/M_T = kt^n \quad (1)$$

where t is time, $M_t$ is the amount of the pharmaceutical agent which has been released at time t, $M_T$ is the total amount of the pharmaceutical agent contained in the tablet, k is a constant, and n is the release kinetics exponent This equation is valid so long as n remains nearly constant. When n is about equal to one, the release of the pharmaceutical agent from the tablet has zero-order kinetics. The amount of pharmaceutical agent released is then directly proportional to the time.

Where the swelling process of the polymer chosen for the excipient is the primary process controlling the drug release (compared to erosion of the swollen polymer), non-zero order release kinetics result. Generally, these release kinetics dictate a value of n approaching 0.5, leading to square-root Fickian-type release kinetics. Accordingly, a polymer must be chosen which will swell and erode readily, to allow erosion resulting in zero-order release kinetics.

Drug release from uncross-linked low molecular weight PEO of MW (molecular weight) equal to about $0.6 \times 10^6$ (laminated films) ensures a constant release rate by achieving synchronized gel thickness. That is, the rate of swelling of the polymer is approximately equal to the rate of erosion of the swollen polymer. On the other hand, the drug release from the high molecular weight PEO of MW=$4 \times 10^6$ is predominantly controlled by the swelling of the polymer rather than the erosion of the polymer. This can result in a non-constant release induced by the diffusion of drugs through the swollen gel layer, especially in high solubility drugs.

Drug release from PEO tablets is governed by swelling/drug diffusion or swelling/polymer erosion depending upon the characteristics of the different molecular weights of the hydrophilic polymers. In order to distinguish between the two mechanisms, swelling experiments involving drug-free tablets of PEO of MWs=$0.9 \times 10^6$, $2 \times 10^6$, and $4 \times 10^6$ were carried out although PEO with a molecular weight of up to $8 \times 10^6$ can also be used with more insoluble drugs. The swollen gel thickness and outer diameter of a drug-free PEO tablet are shown in FIG. 1. FIG. 1 shows that a constant gel thickness is obtained with the PEO tablets of MWs=$0.9 \times 10^6$ and $2 \times 10^6$, whereas the swollen gel thickness from the PEO tablet of $4 \times 10^6$ keeps increasing with time.

As can be seen from FIG. 1, in the early time of the swelling/erosion process, the overall size of the tablet along with the gel layer increases rapidly due to the immediate swelling of the PEO tablet. The swelling rate of the polymer equals the dissolution rate of the swollen polymer gel, resulting in the synchronization of the gel layer thickness.

The release kinetics of the tablet are also dictated by the pharmaceutical agent itself. A drug which is highly soluble will tend to be released faster than drugs which have low solubility. Where a drug has high solubility, polymer swelling and erosion must take place rapidly to maintain zero order release kinetics. If the swelling and erosion take place too slowly, the swelling process of the polymer is the primary process controlling the drug release (since the drug will diffuse from the swollen polymer before the polymer erodes). In this situation, non-zero order release kinetics result. As a result, the administration of a highly soluble pharmaceutical agent requires a relatively rapidly swelling and eroding excipient. To use such a material to produce a tablet which will last for 24 hours can require a large pill.

To overcome this difficulty, a doughnut-shaped tablet with a hole though the middle can be used with a less rapidly swelling and eroding polymer. With such a tablet, the surface area of the tablet increases as the tablet erodes. This exposes more polymer, resulting in more polymer swelling and erosion as the tablet shrinks in size. The type of tablet can also be used with very highly soluble pharmaceutical agents to maintain zero order release kinetics.

Conversely, the delivery of an insoluble pharmaceutical agent is dictated only by the erosion of the swollen polymer layer, since there will be no diffusion and dissolution of the pharmaceutical agent out of the swollen polymer matrix. Accordingly, relatively slow swelling and eroding polymers can be used. In this case, if a sufficiently slow polymer is used, a tablet can be made very small with a higher concentration of pharmaceutical agent than would be used in a normal-sized tablet. This would result in a very small but very effective sustained release tablet.

EXAMPLE

POLYOX-WSR NFs (non-crosslinked polyethylene oxide) of average molecular weight of $0.9 \times 10^6$, $2 \times 10^6$ and $4 \times 10^6$ and $5 \times 10^6$, and polyethylene glycol (PEG8000) were obtained from Union Carbide Corporation (Danbury, Conn.). Theophylline anhydrous U.S.P. and magnesium stearate U.S.P. were obtained from Amend Co. (Irving, N.J.) and Mallinckrodt Chemical (Jersey City, N.J.), respectively. Diltiazem HCl, nifedipine, diclofenac sodium, sulfathiazole, casein and gelatin Type B (75 bloom) were obtained from Sigma Chemical Co. (St. Louis, Mo.). Hydroxypropylmethylcellulose was obtained from Dow Chemical (Midland, Mich.) and Shin-Etsu Chemical Co., Ltd. (Tokyo, Japan). The materials were used as received.

Sodium lauryl sulfate U.S.P., soybean lecithin granules, and tragacanth U.S.P. were obtained from Amend Co. (Irving, N.J.). Acacia (Arabic gum) was purchased from Aldrich Chemical (Milwaukee, Wis.). $\beta$-cyclodextrin and hydroxypropyl-$\beta$-cyclodextrin were obtained from Amazio (Indianapolis, Ind.). Procardia XL™ tablets (30 mg and 60 mg) are available from Pfizer (New York, N.Y.)

The ingredients (PEO, drug, magnesium stearate, and other additives) were homogeneously mixed and then tableted using a single punch tablet machine (Stokes Model F, Philadelphia, Pa.). A set of tablet punches with flat surfaces were used to prepare tablets of various diameters, including 7 mm, 8.1 mm, 9.5 mm, and 11 mm. They were charged with the formulation, and the compression of 2000 to 4000 pounds was exerted by turning over the machine by hand. The hardness of the resulting tablets was 5.5 to 7.0 Kp (Schleuniger Model 2E/106, Switzerland). The resulting tablets weighed about 160 mg.

Solubilizers and emulsifiers were also included in several of the tablet formulations.

In vitro release of drugs from the different formulation tablets was carried out by using the USP basket procedure in distilled/deionized water at a stirring rate of 100 rpm and 37° C., if not otherwise stated. Theophylline and diltiazem HCl were chosen as model drugs. The release of theophylline and diltiazem HCl was assayed by a HP\8252A (Hewlett Packard Corporation) diode-array spectrophotometer at 244 nm and 266 nm, respectively. The release kinetic data (up to 60% release) were treated by equation (1) above. After this point, frequently n was no longer constant, and therefore equation (1) did not apply.

In addition, the release kinetics of diclofenac sodium, salicylic acid, sulfathiazole, sulfapyridine and nifedipine were assayed by a HP\8252A diode-array spectrophotometer at 250 nm, 244 nm, 268 nm, 288 nm, and 340 nm, respectively.

According to the criteria for release kinetics from a swellable matrix (cylindrical shape), zero-order and anomalous transport kinetics are represented by 0.89 <n<1.0 and 0.45<n<0.89, respectively. A linear regression analysis (Microsoft Excel 5.0) of the logarithmic form of equation (1) was carried out with $R^2 \geq 0.99$.

Both circular faces of the cylindrical tablet were covered with two transparent Mylar sheets, fixed onto the bases via an epoxy glue. The covered tablet was then introduced into water as a dissolution medium. The tablet was withdrawn periodically, and the moving boundaries both at the glassy/rubbery interface and at the matrix/dissolution medium interface were measured via a stereo microscope (Olympus SZ60) with a measuring device attachment. The tablet was then returned to the bath.

As can be seen from FIG. 1, the synchronization of the gel layer thickness takes place earlier with the low molecular weight PEO and shortly after the outer diameter starts becoming smaller. The higher the molecular weight, the later the synchronization takes place. However, for a higher molecular weight PEO tablet ($4 \times 10^6$) the synchronization of the gel layer did not occur and the gel layer thickness increased until the entire tablet was in gel form. After the front meets at the core of the tablet, the swollen PEO gel lasts a much longer time than other swellable/erodible polymers such as PMMA/MAA and PVA. The swollen PEO gel layer can last 2 to 4 hours depending upon the molecular weight of the PEO. As a result of this long residence time of the gel layer, it is expected that the release kinetics are governed by the erosion/drug diffusion process after the swelling front meets at the core of the tablet.

Figure 2:
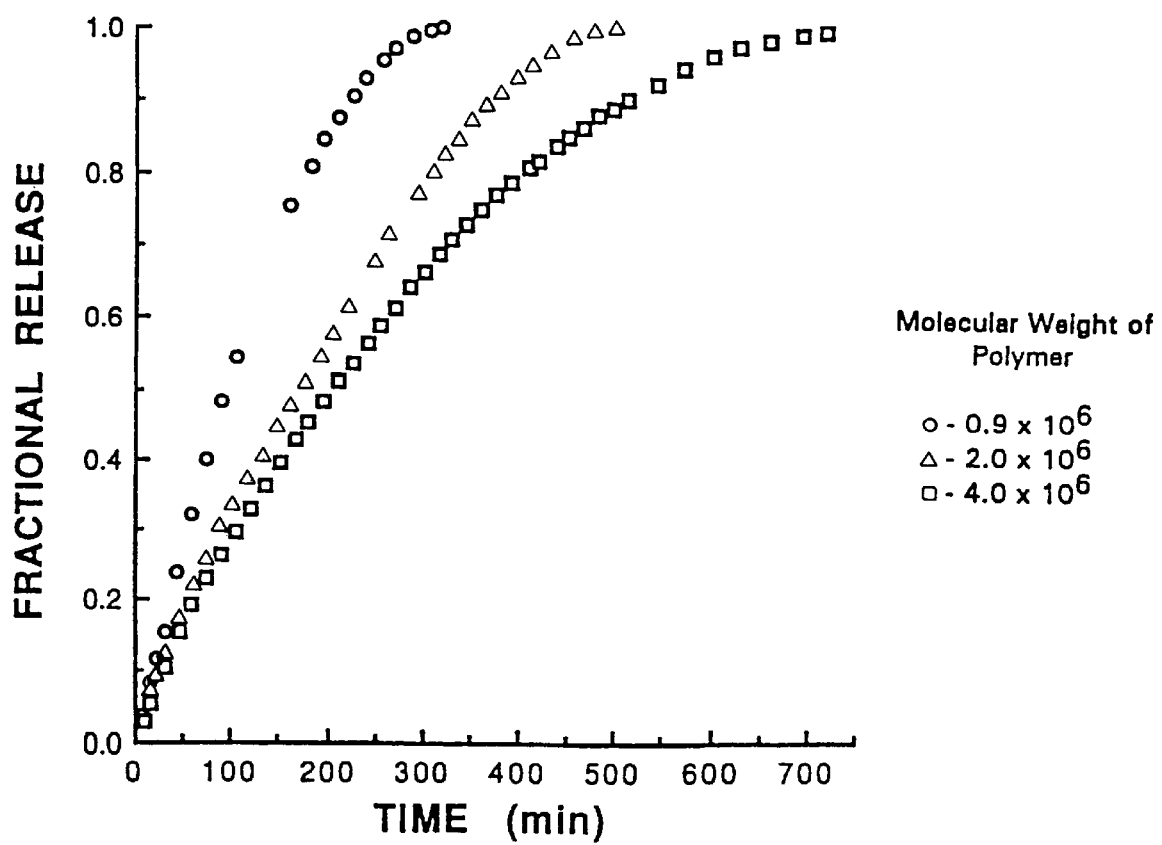
FIG. 2 is a graph of the fractional release of theophylline from PEO tablets versus time, for various molecular weights of PEO polymer.

FIG. 2 shows the effect of PEO molecular weight on drug release of theophylline from tablets. The rate of dissolution (erosion) of hydrophilic polymers decreases with increasing molecular weight. This causes different molecular weights of PEO to have different values for the release exponent (n). For the release of theophylline from PEO tablets, the value of the release exponent (n) was 0.99 (±0.024), 0.80 (±0.004), and 0.83 (±0.019) for tablets formed from PEO having molecular weights of $0.9 \times 10^6$, $2 \times 10^6$, and $4 \times 10^6$, respectively. The lower molecular weight PEO (MW=$0.9 \times 10^6$) tablet exhibits a constant release rate, whereas the release rate from PEO tablets having molecular weights of $2 \times 10^6$ and $4 \times 10^6$ may vary, depending on the solubility of the drug used.

Accordingly, the synchronized gel thickness plays an important role on the release kinetics at the early time of drug release. As the molecular weight of the polymer increases, the dissolution rate of the polymer decreases compared to the swelling rate of the polymer. The "dissolution rate" and the "erosion rate" are used here interchangeably. In actuality, the decrease in the size of the swollen gel layer is due both to erosion and dissolution. Due to the low dissolution rate, the thickness of the polymer layer increases. Drug diffusion through the swollen gel layer then becomes the foremost process controlling the release mechanism. With high molecular weight (or high viscosity grade) polymers of PEO and HPMC, the swelling of the polymer is the dominant step in controlling release kinetics over the erosion of swollen polymer. With low molecular weight polymers of PEO and HPMC, the erosion of the polymer is the rate determining step for the release kinetics. However, the degree of swelling of PEO is higher than HPMC resulting in more favorable kinetics for PEO than for HPMC.

Figure 3:
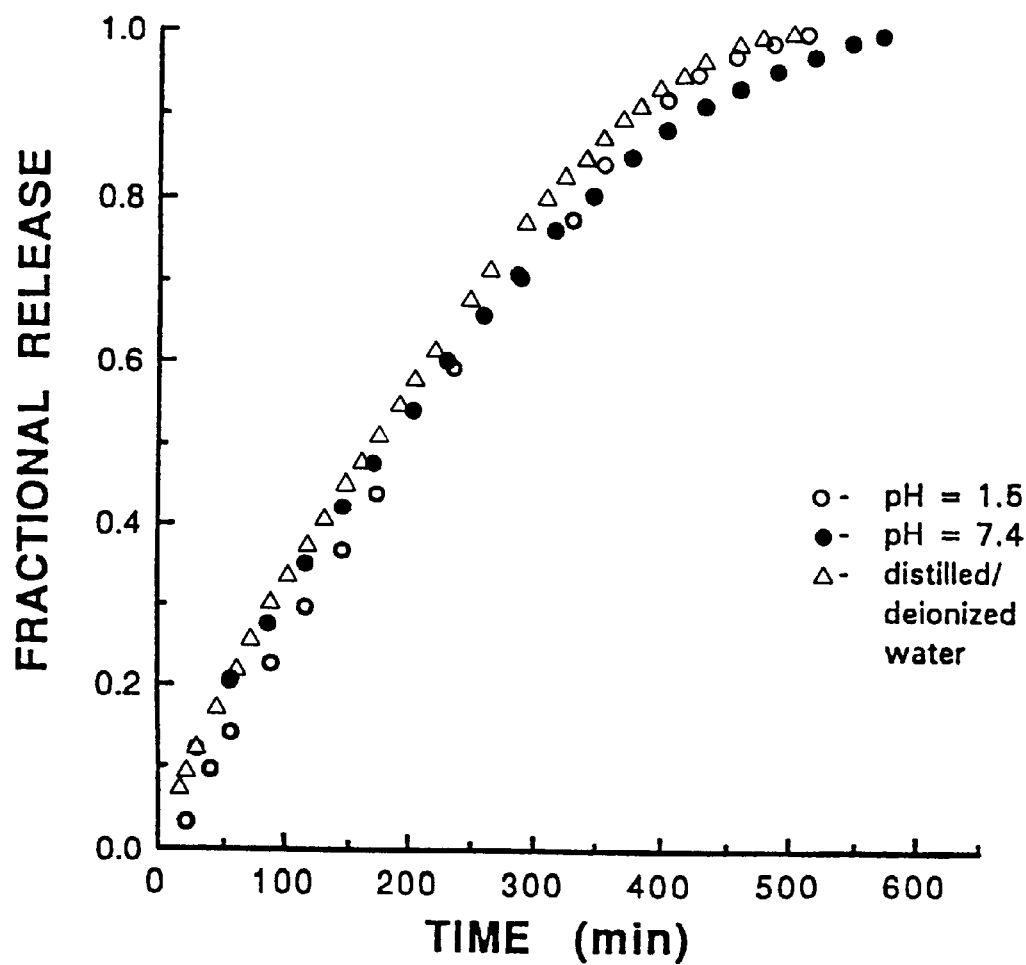
FIG. 3 is a graph of the fractional release of theophylline from PEO tablets versus time at varying pH levels.

The release of theophylline from PEO tablets is not significantly influenced by the pH variation of the dissolution medium, as shown in FIG. 3. Therefore PEO may be a good candidate for oral drug delivery systems because oral dosage forms travel along the gastrointestinal tract in which the pH changes from an acidic environment (pH<2) in the stomach to a weak base (pH about 8) in the intestines.

Figure 4:
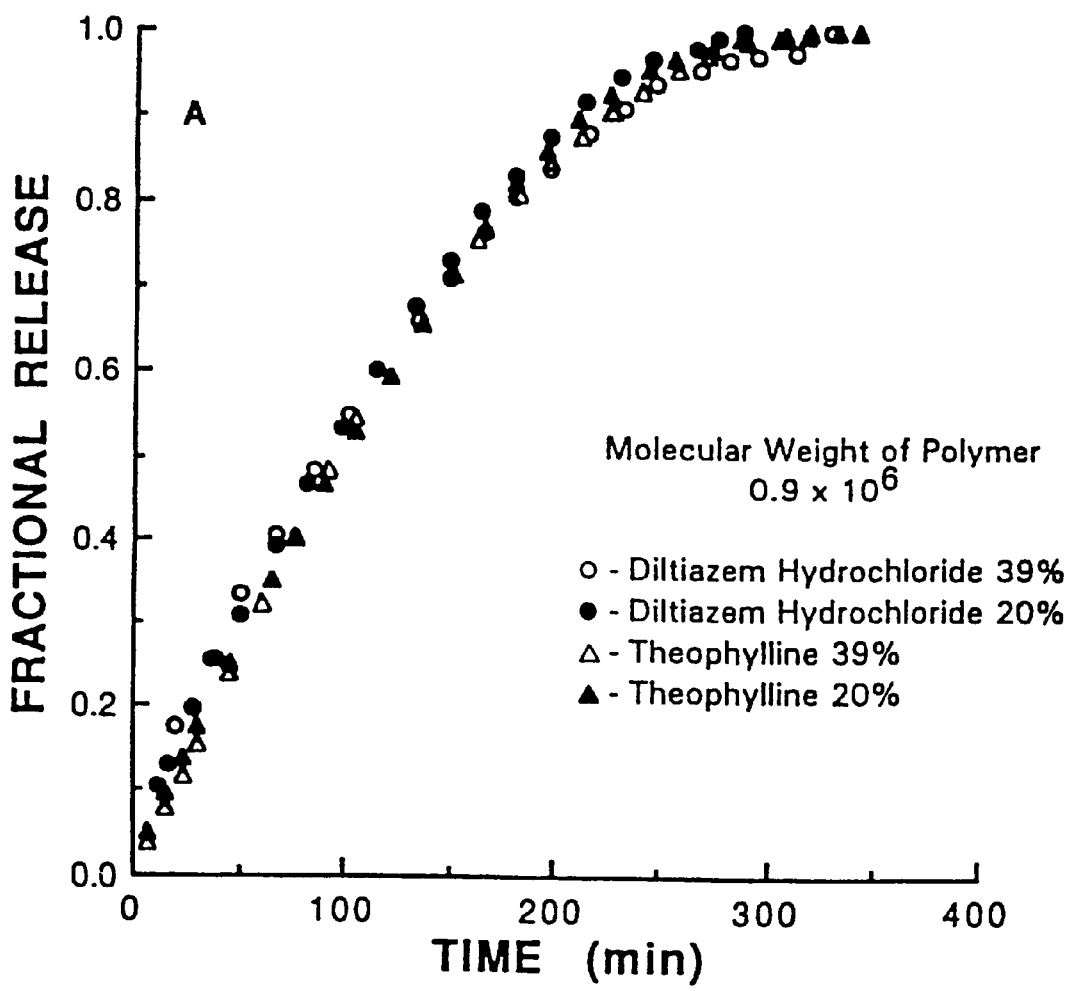
FIG. 4 is a graph of the fractional release of theophylline and diltiazem hydrochloride from $0.9 \times 10^6$ molecular weight PEO tablets versus time for varying drug loadings.
Figure 5:
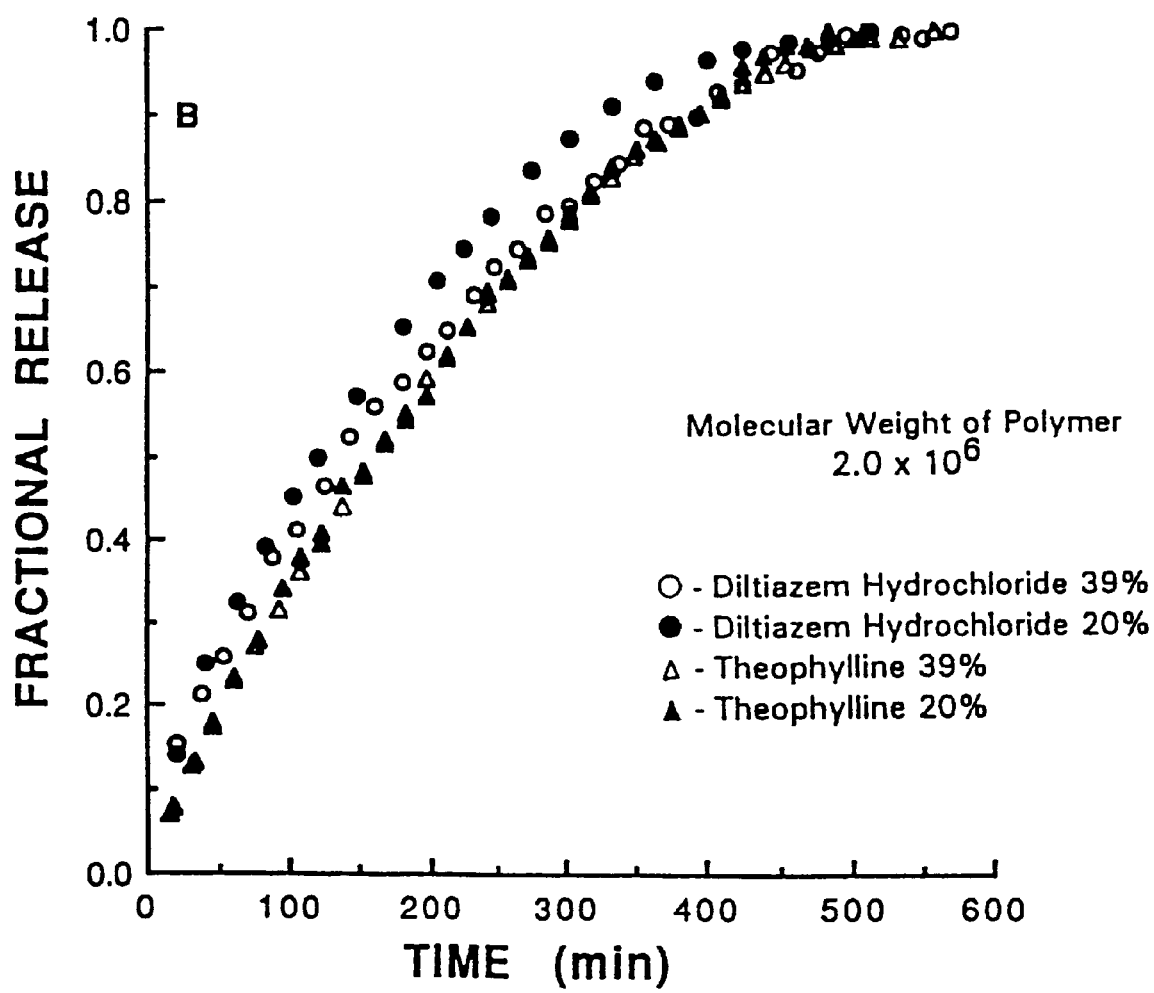
FIG. 5 is a graph of the fractional release of theophylline and diltiazem hydrochloride from $2.0 \times 10^6$ molecular weight PEO tablets versus time for varying drug loadings.

PEO tablets having varying loadings of pharmaceutical agents were tested to determine the effect of loading on the release kinetics. The results are shown in FIGS. 4 and 5. No significant difference in release rate was observed with the different drug loadings in PEO tablets.

The release kinetics of PEO tablets of MW=$0.9 \times 10^6$ remain unchanged with the exponent n ranging from 0.90 (±0.016) to 0.99 (±0.024) even though the drug loading is increased. Even for PEO tablets of MW=$2 \times 10^6$, the release profiles of theophylline from 20% and 39% loaded tablets are superimposed with the exponent n ranging from 0.80 (±0.004) to 0.82 (±.007). In these cases, the diffusion of theophylline (<1.0% solubility in water) through the swollen gel layer does not play an important role in the release mechanism in PEO tablets. Rather it is the rate of erosion of the gel layer which dictates the rate of release of the drug.

Figure 6:
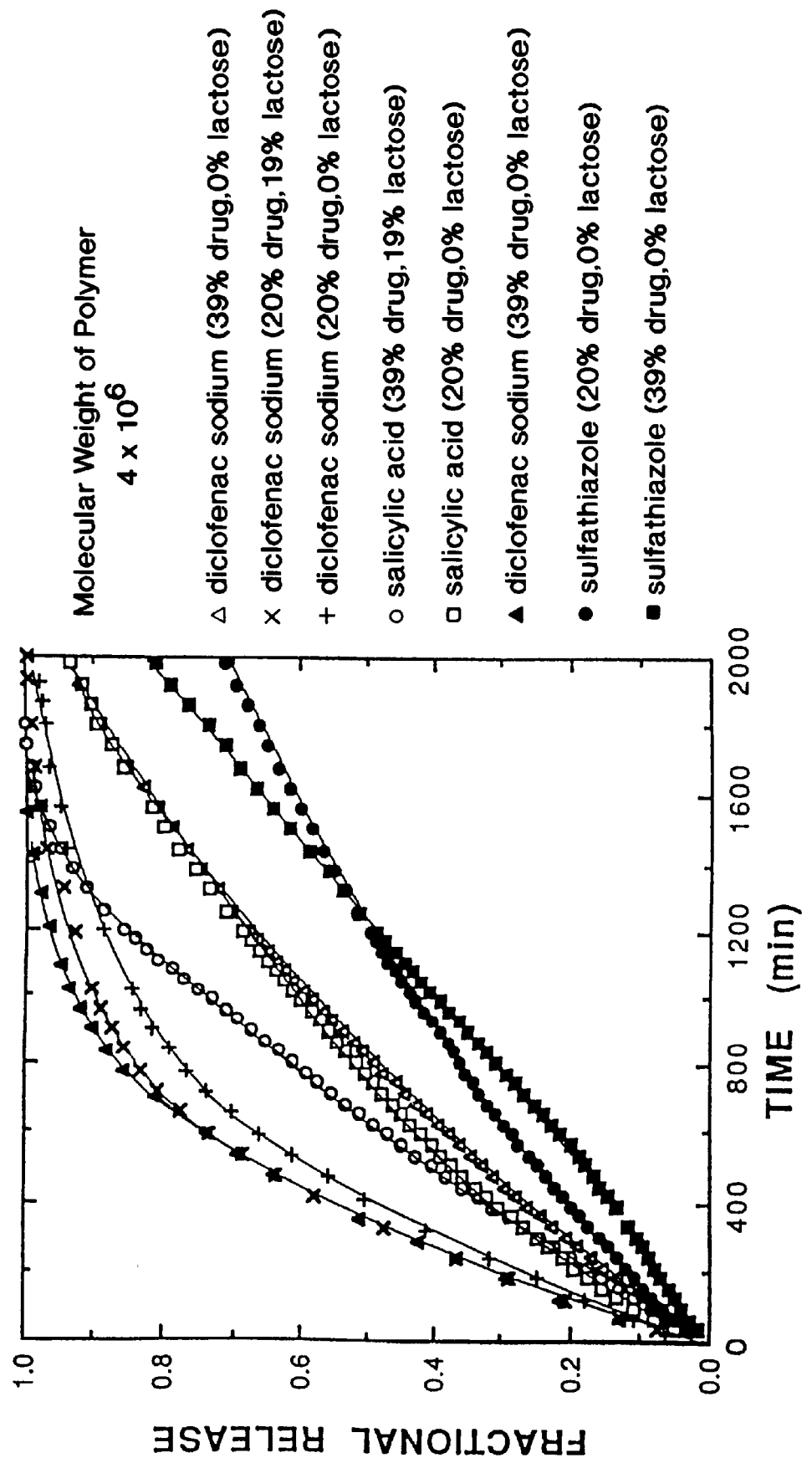
FIG. 6 is a graph of the fractional release of diclofenac sodium, salicylic acid and sulfathiazole from $4 \times 10^6$ molecular weight PEO tablets versus time for various drug loadings and water soluble additives.

Similarly as exhibited in FIG. 6 the release kinetics of high solubility drugs from PEO tablets having a molecular weight of $4 \times 10^6$ were not affected by drug loading. A set of tablet punches with flat surfaces were used to prepare the tablets having diameters of 11.1 mm and weights of 550 mg except for the sulfathiazole tablets which were 9.5 mm in diameter and weighed 400 mg. All the tablets were compressed to 4000 pounds. As drug loading increased from 20% to 39%, the linearity of the release kinetics of highly water soluble drugs such as diclofenac sodium did not significantly change. However, the time period of release did vary.

As drug loading increased from 20% to 39% in the $4 \times 10^6$ MW tablets, the release kinetics exponent n for low solubility drugs such as salicylic acid and sulfathiazole changed from 0.72 and 0.78, to 0.81 and 0.94, respectively at the higher loading level. The higher number indicates the drug release rate was closer to zero order. This observation also was shown with respect to PEO tablets having molecular weights of $0.9 \times 10^6$ and $2 \times 10^6$. These results indicate that diffusion plays a more important role in the release kinetics of lower solubility drugs at the 20% loading level (where the majority of drug in the polymer matrix is in the dissolved state) than at the 39% loading level where less of the drug is in the dissolved state.

FIG. 6 also shows the effect of a water soluble excipient (lactose) on drug release kinetics. A water soluble excipient mixed with the polymer matrix reduces the polymer content and enhances the hydration of the polymer through osmotic pressure. The addition of lactose did not significantly affect the release kinetics other than to shorten the period of release. The release kinetics, however, of diclofenac sodium from a PEO tablet having a molecular weight of $4 \times 10^6$ with 39% drug loading are superimposable (except for the final stage of release) with the release kinetics from a PEO tablet containing 20% drug and 19% lactose, provided that each tablet has the same total weight. This indicates that the addition of a water soluble excipient may increase the time of release of higher solubility drugs at lower drug loadings.

The diffusion of water into the polymer matrix is not greatly facilitated by the water uptake of drugs but rather by the water uptake of the hydrophilic polymer. This demonstrates that the swelling/erosion of the polymer is the controlling variable rather than the diffusion of drugs through the swollen gel layer. This may not be true when a highly water-soluble drug (diltiazem HCl, solubility>50%) is employed. FIGS. 4 and 5 show the effect of drug solubility on the release of drugs from PEO tablets. With a low molecular weight PEO, the solubility of the drug does not markedly affect the release of drugs from PEO tablets as may occur with other hydrophilic polymers.

Figure 7:
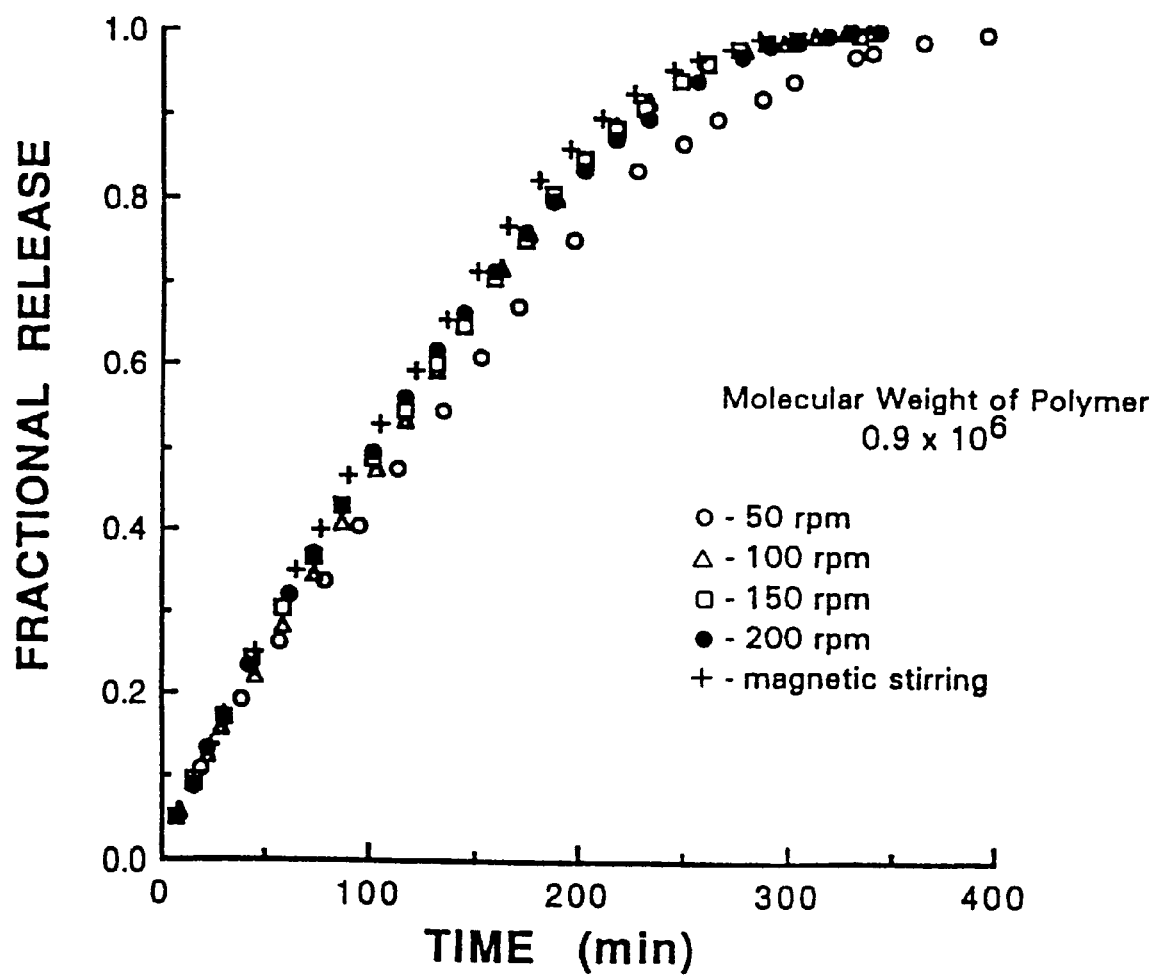
FIG. 7 is a graph of the fractional release of theophylline from $0.9 \times 10^6$ molecular weight PEO tablets versus time for various rates of agitation.

PEO tablets were also tested to determine the effect of stirring on the release of a drug from the tablet. The results are shown in FIG. 7. As may be seen from FIG. 7, the rate of release of the drug from the PEO tablet increased as stirring was increased with an increase in the stirring rate from 50 to 100 rpm. However, above 100 rpm, the rate of release of the drug was insensitive to the amount of stirring. The insensitivity of PEO tablets to the stirring rate also makes PEO a good candidate for oral dosage forms since the release rate will not vary as the tablet is subjected to turbulence in the stomach and intestine.

Figure 8:
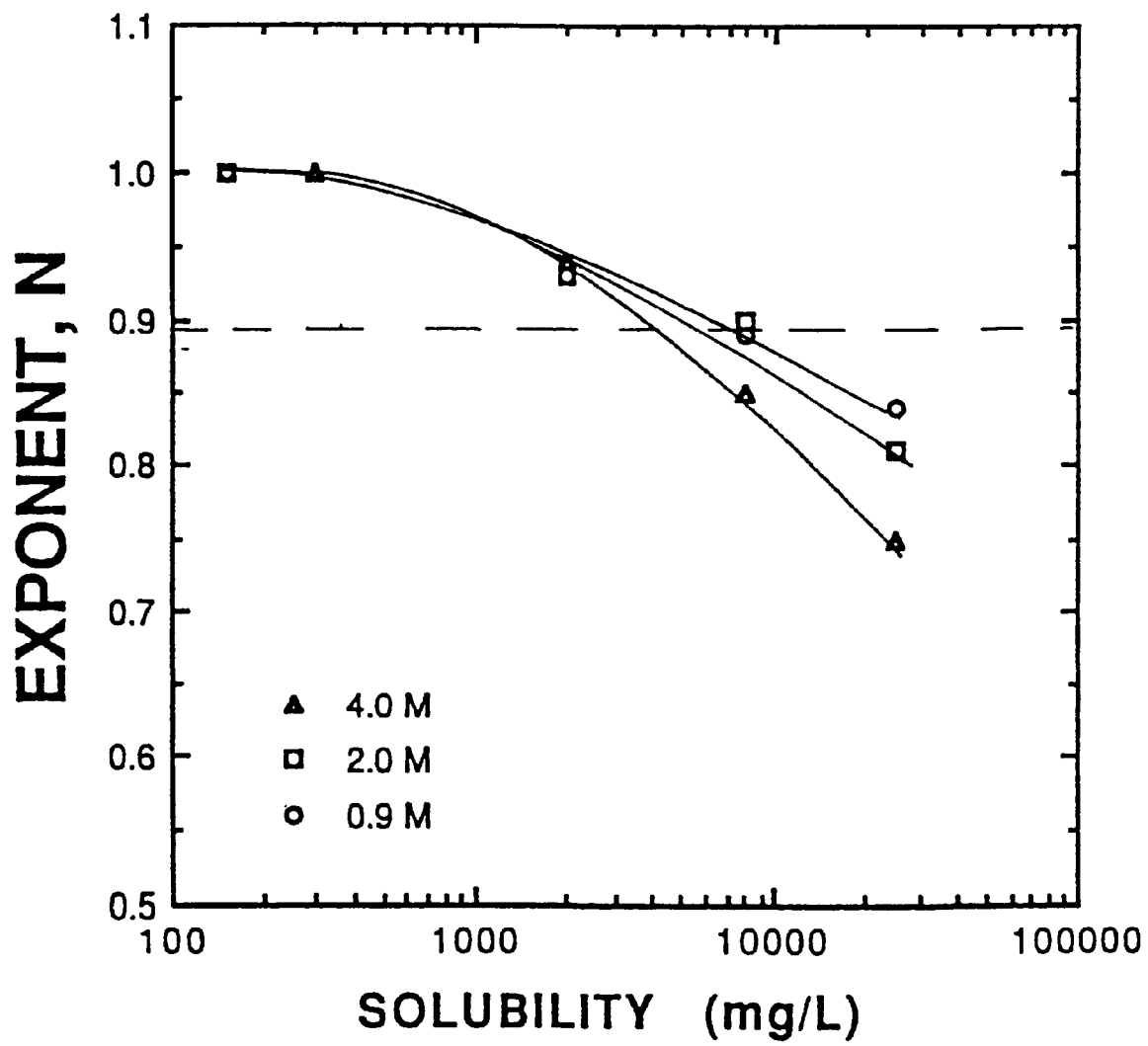
FIG. 8 is a graph of the release exponent (n) versus solubility of the drug for tablets of PEO of various molecular weights.

The change in release constant with solubility of the drug is shown in FIG. 8. As the solubility of the drug increases, diffusion from the gel layer increases. Where the erosion of the gel layer is not fast enough to keep up with the diffusion, n decreases indicating non-constant release. As would be expected, this occurs more readily in higher molecular weight polymers.

Figure 9:
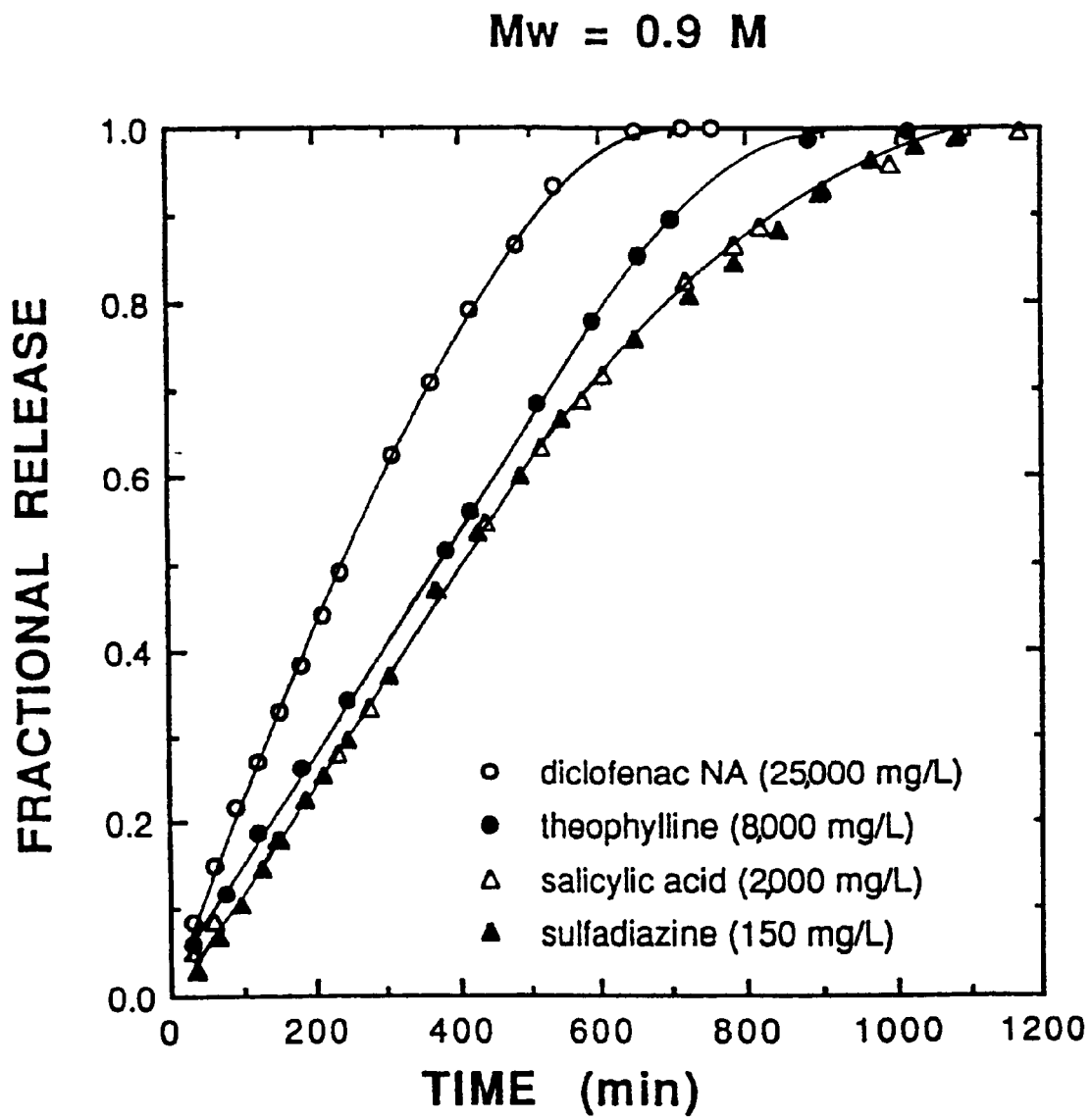
FIGS. 9 and 10 are graphs of the fractional release of various drugs versus time from tablets of $0.9 \times 10^6$ molecular weight PEO.
Figure 11:
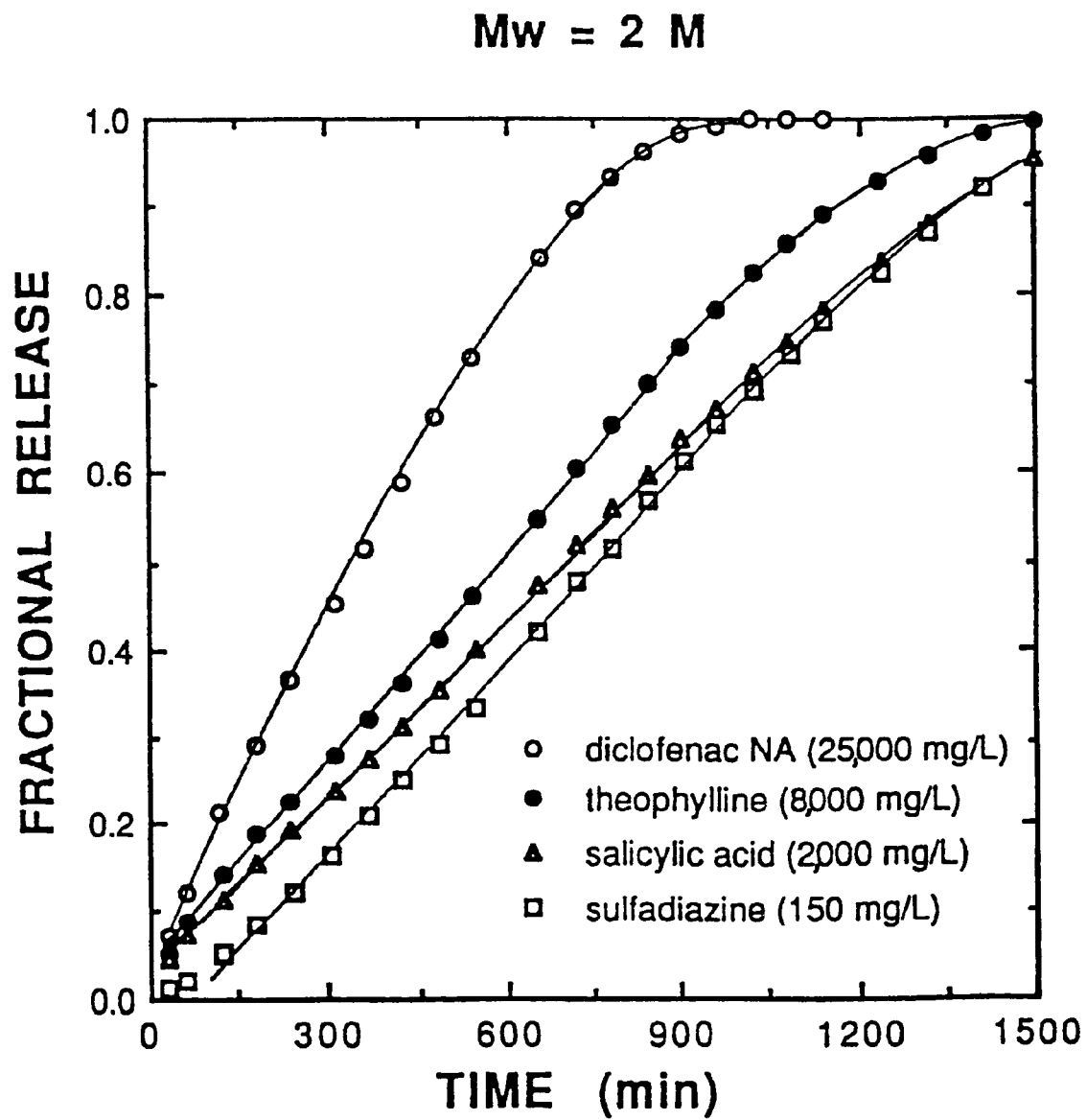
FIGS. 11 and 12 are graphs of the fractional release of various drugs versus time from tablets of $2.0 \times 10^6$ molecular weight PEO.
Figure 13:
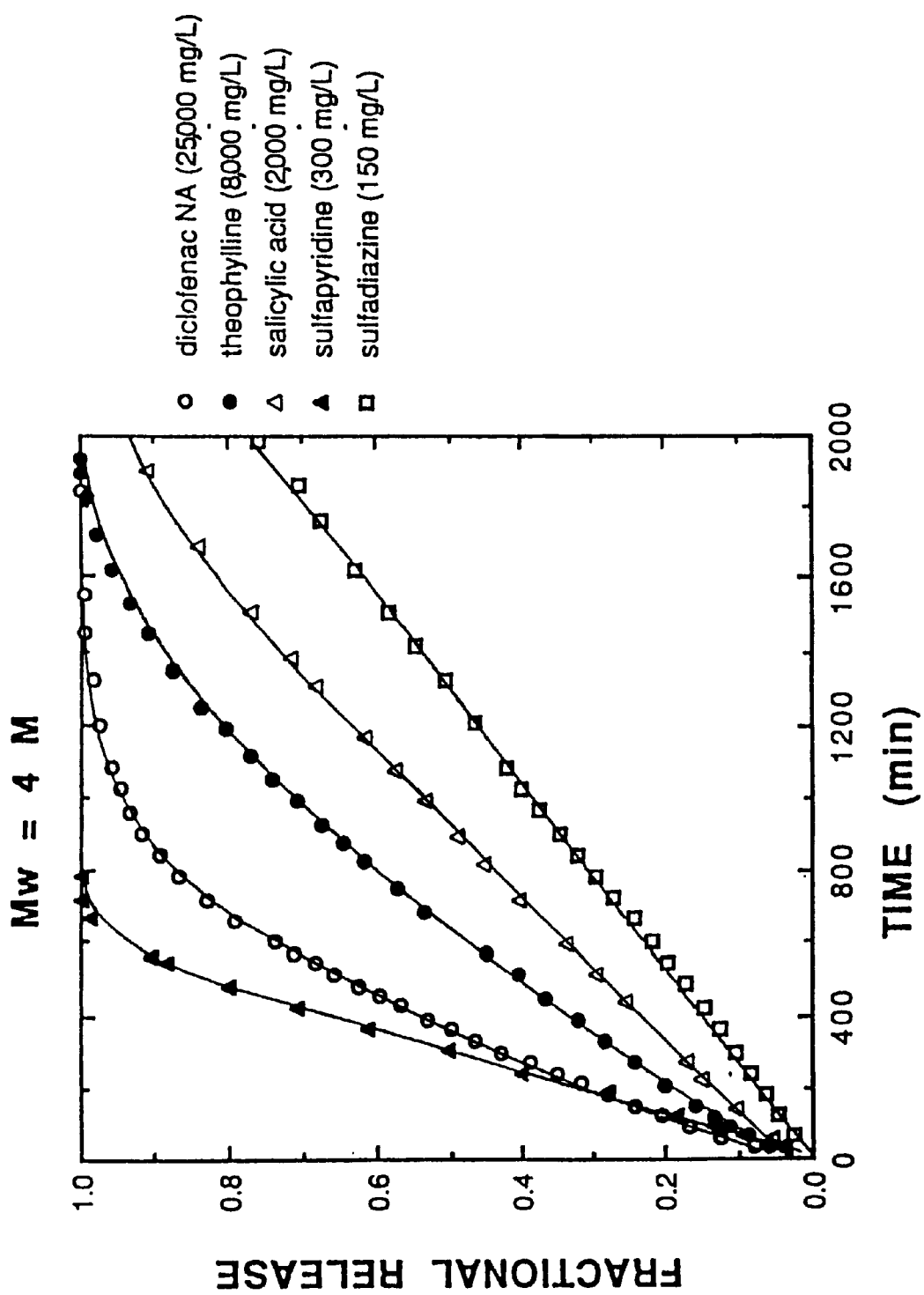
FIGS. 13 and 14 are graphs of the fractional release of various drugs versus time from tablets of $4.0 \times 10^6$ molecular weight PEO.

This effect is further demonstrated in FIGS. 9, 11, and 13. There, the particular drugs used for testing are shown along with their typical solubilities. The most constant release over the longest period of time is exhibited by sulfadiazine, the drug with the lowest solubility. The least constant release is exhibited by the more soluble drugs such as diclofenac sodium and theophylline. The non-constant release worsens with higher molecular weight polymers.

Figure 10:
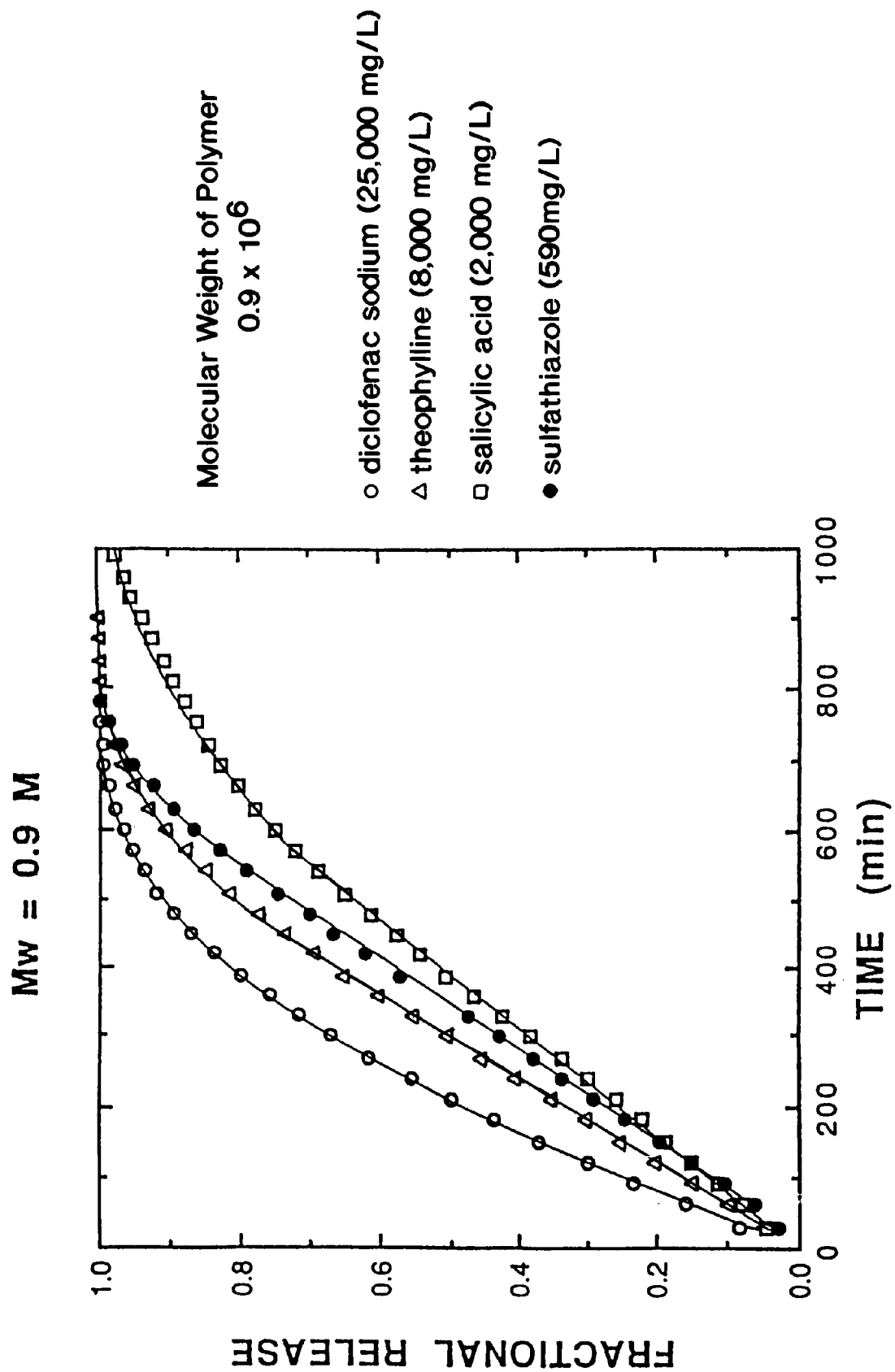
Figure 12:
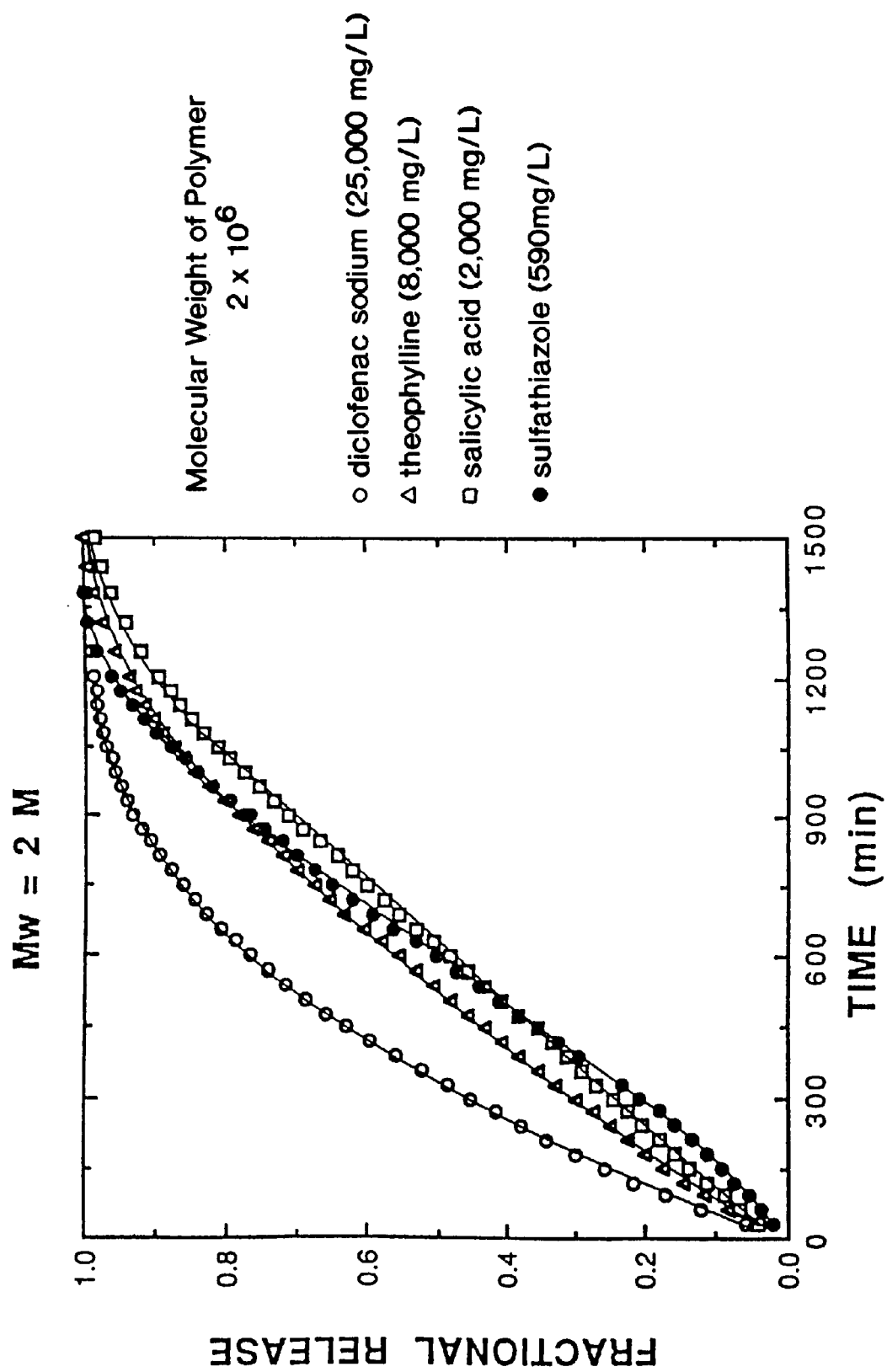
Figure 14:
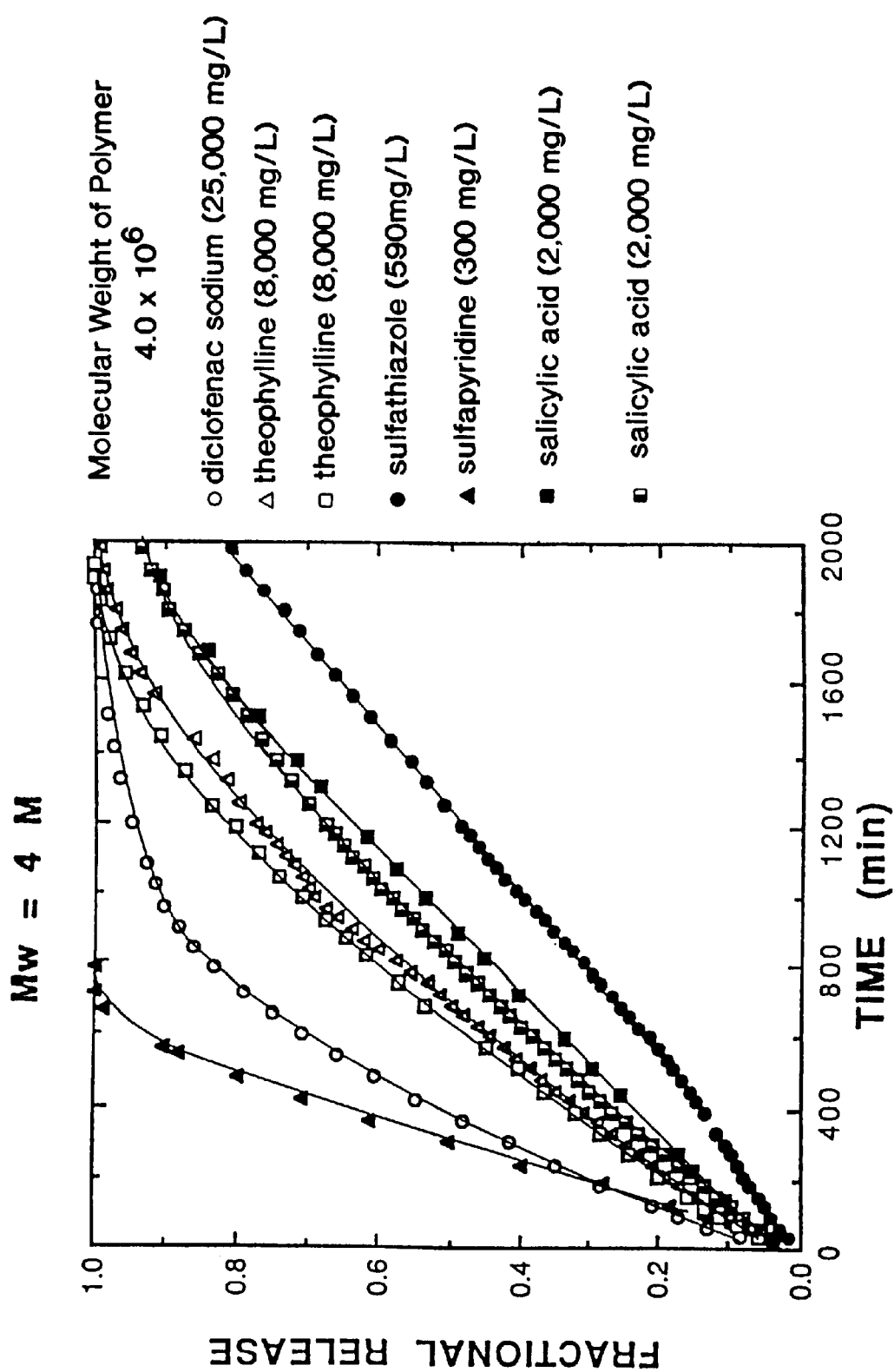

Similarly, FIGS. 10, 12 and 14 show particular drugs used for testing with their typical solubilities. A set of tablet punches with flat surfaces were used to prepare the tablets having diameters of 11.1 mm and weights of 550 mg except for the sulfathiazole tablets which were 9.5 mm in diameter and weighed 400 mg. The tablets were compressed to 4000 pounds. Constant release rates over the longest period of time were exhibited by sulfathiazole and salicylic acid, drugs with low solubilities, from PEO tablets having molecular weights of $0.9 \times 10^6$, $2 \times 10^6$ and $4 \times 10^6$. A slightly sigmoidal profile was observed for sulfathiazole. The release kinetics exponent n for salicylic acid and sulfathiazole ranged from 0.81 to 0.97 and 0.96 to 1.17, respectively, decreasing slightly with increasing polymer (PEO) molecular weight.

The drugs having higher solubilities such as theophylline and diclofenac sodium also exhibited constant or near constant release kinetics n, although somewhat less constant than the release rates of the low solubility drugs from these PEO tablets. For example, the release kinetics exponent n for diclofenac sodium and theophylline ranged from 0.72 to 0.91 and 0.79 to 1.01, respectively, decreasing slightly with increasing PEO molecular weight. Any non-constant release worsens with increasing molecular weights. As may be seen from FIG. 14, the low solubility drug sulfapyridine also exhibited constant release kinetics having a release kinetics exponent n of 1.10. The period of release, however, was relatively short. This may have resulted from the sulfapyridine forming an associate complex with the PEO as evidenced by lower swelling of the polymer.

Figure 15:
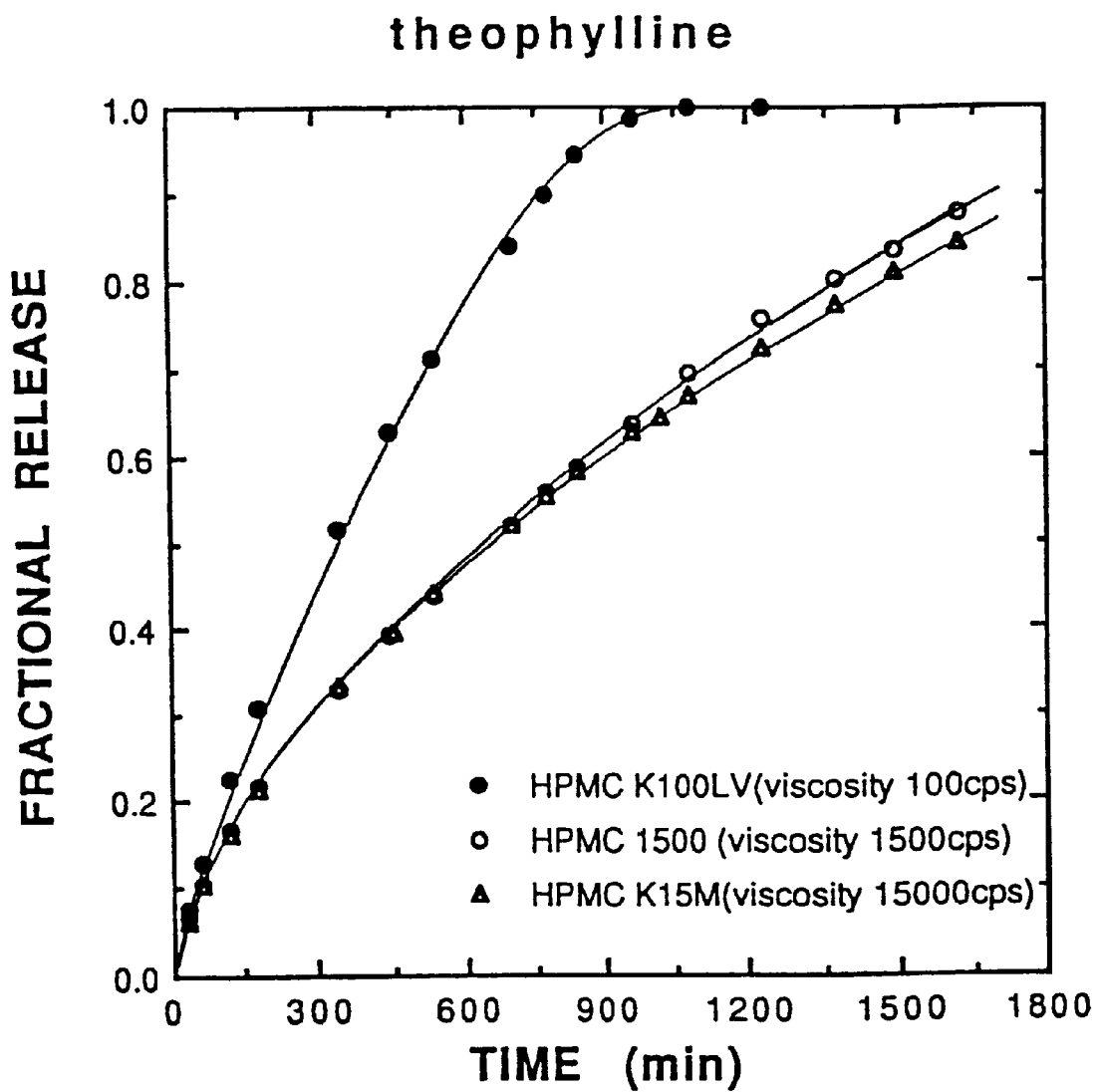
FIG. 15 is a graph of the fractional release of theophylline versus time from tablets formed from hydroxypropylmethylcellulose of varying viscosity.
Figure 16:
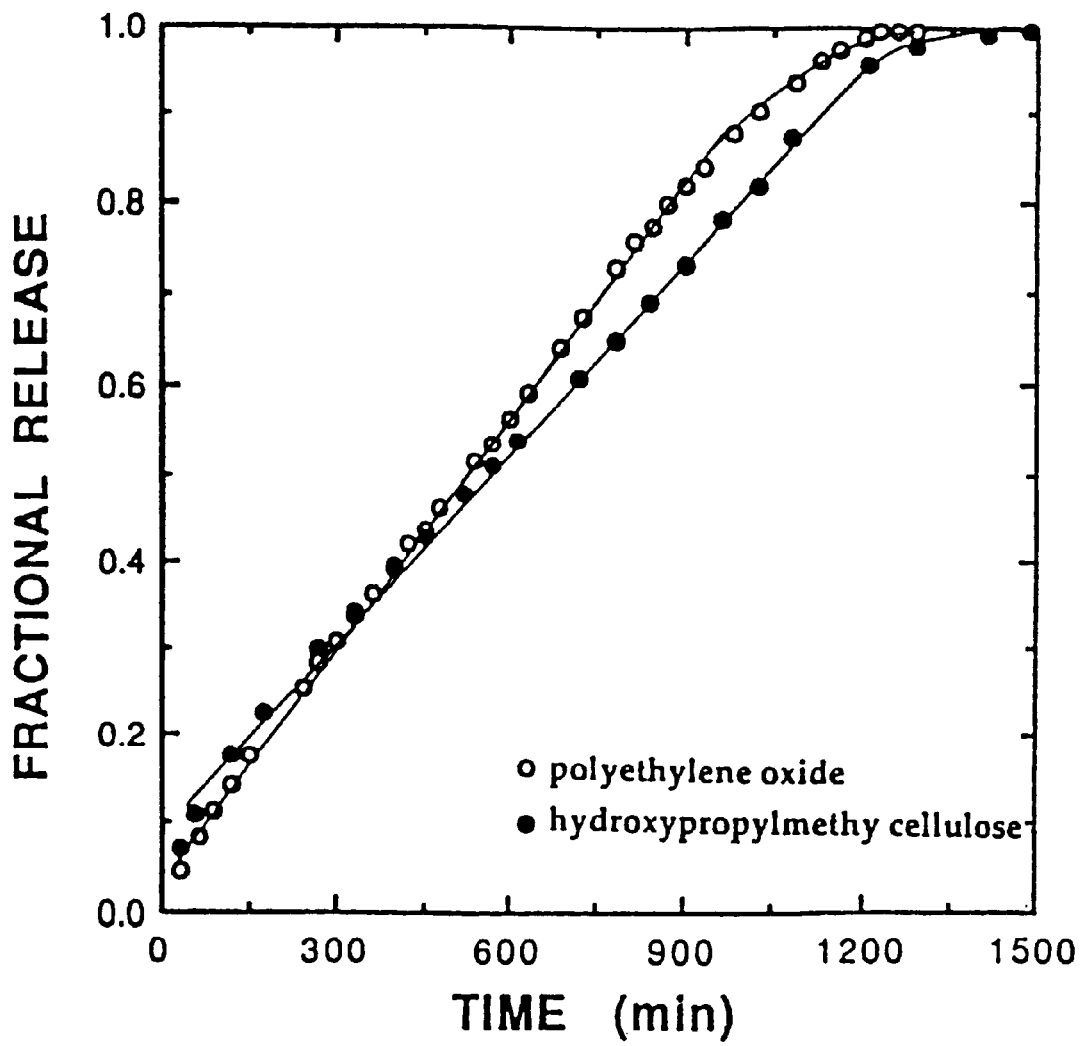
FIG. 16 is a graph of the fractional release of theophylline from tablets of PEO having a molecular weight of $4.0 \times 10^6$ and from tablets of HPMC having a viscosity of 1500–1800 centipoise and having a hole through the center thereof.

Release of lower solubility drugs from tablets of PEO having a molecular weight of $4 \times 10^6$ is controlled by dissolution of the drug. Upon contact with water, the PEO polymer swells with the swollen front penetrating toward the core of the polymer matrix. The drug (mostly in undissolved form) becomes suspended in the dissolution medium within the polymer matrix. This is followed by erosion of the polymer and dissolution of the drug in the dissolution medium. A small amount of the drug is dissolved and released directly from the polymer matrix by diffusion. FIG. 15 shows some linearity of drug delivery with HPMC, particularly where a low viscosity HPMC is used. HPMC having a viscosity of up to 100,000 centipoise can also be used with the present invention. However, as shown by FIG. 16, the results achieved are improved substantially by the formation of a hole in the tablet. Forming a hole in the tablet allows the surface area of the tablet to increase as the tablet dissolves. This increases the amount of polymer which is exposed to the environment, and thus increases the amount of polymer which swells. This increases the dissolution rate of the polymer which makes the drug administration rate linear. This improves performance provided the hole in the tablet is not so small as to substantially disappear from the swelling which occurs when the tablet is first contacted with moisture.

Figure 17:
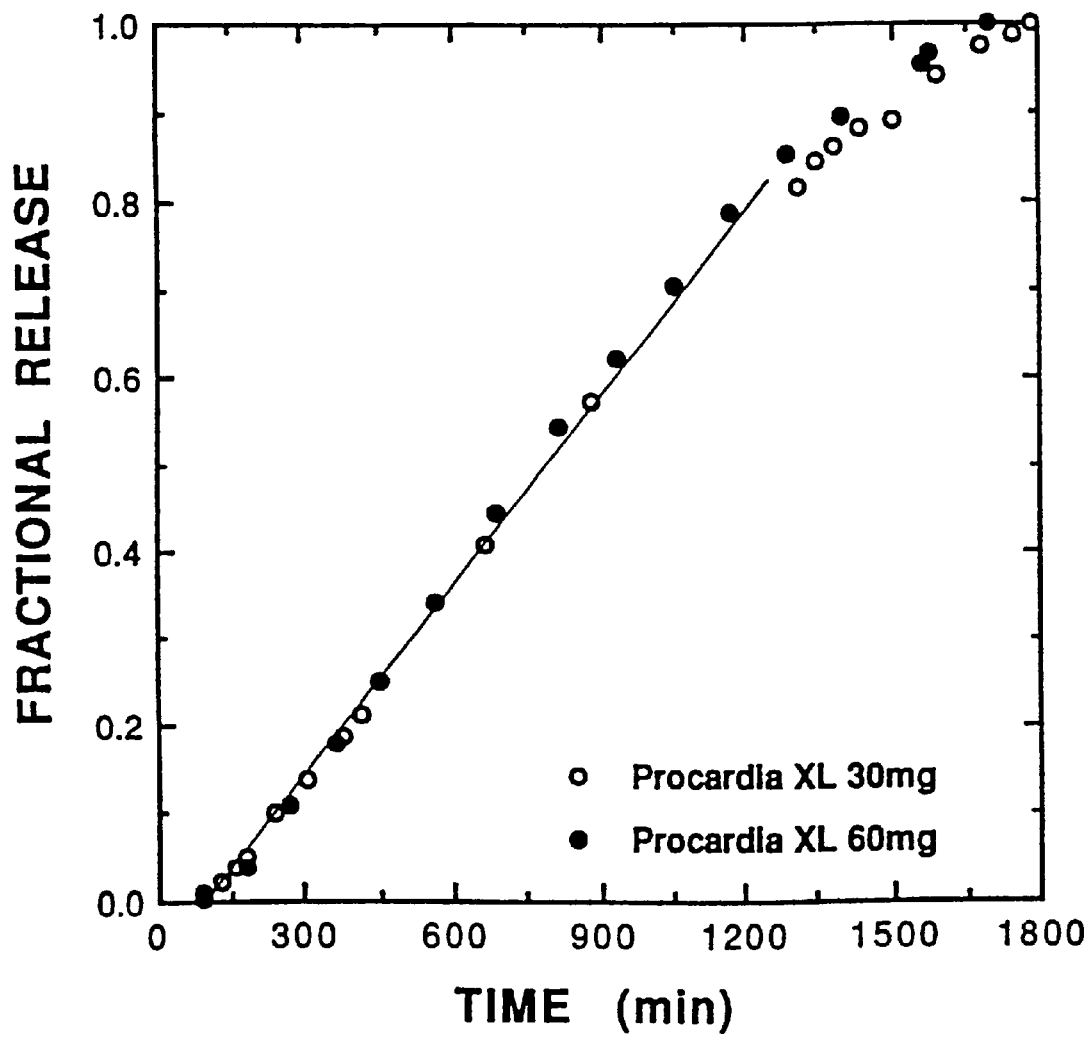
FIG. 17 is a graph of the fractional release from Procardia XL™ tablets having 30 mg and 60 mg of drug per tablet.
Figure 18:
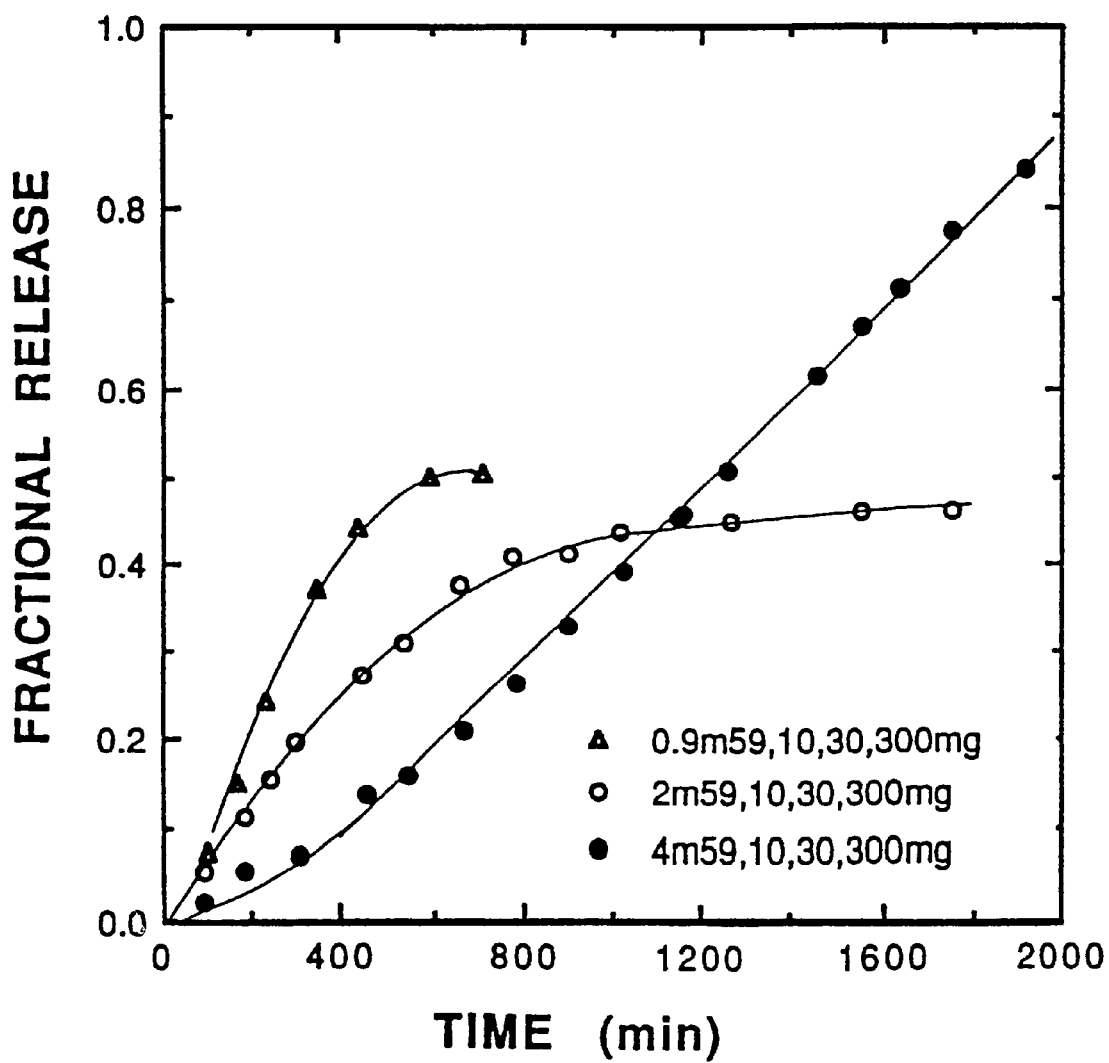
FIG. 18 is a graph of the fractional release of nifedipine from tablets of PEO having various molecular weights and having 10 percent nifedipine.
Figure 19:
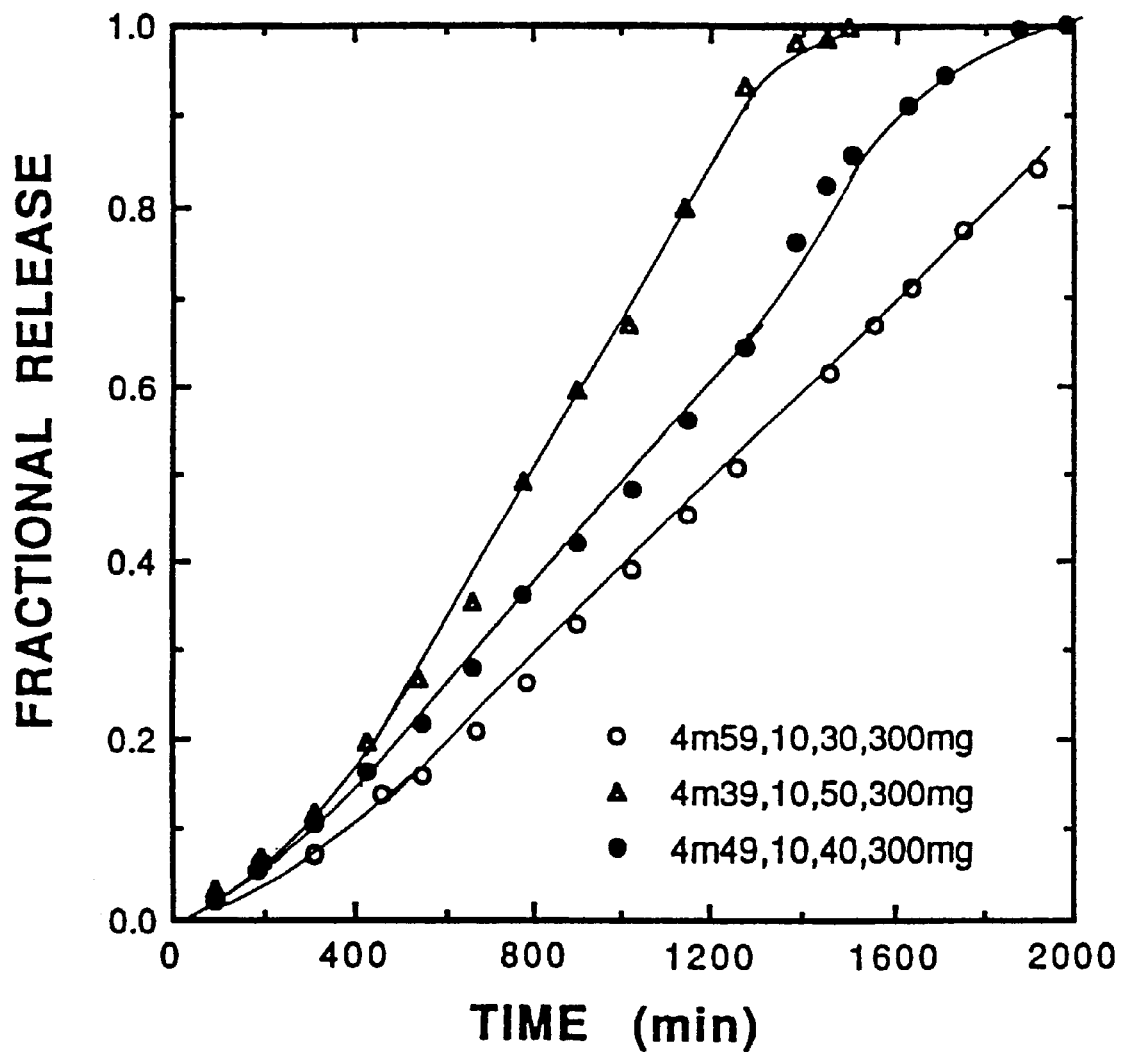
FIG. 19 is a graph of the fractional release of nifedipine from tablets of PEO having a molecular weight of $4.0 \times 10^6$ and having various amounts of polyethylene glycol added thereto.

FIG. 17 shows the release characteristics of Procardia XL™ nifedipine tablets of 30 and 60 milligrams (Pfizer, Inc., New York, N.Y.). This figure may be compared to FIGS. 18–25 and 25–31, which show nifedipine tablets having various compositions made in accordance with the present invention. The compositions of the tablets tested in FIGS. 18, 19, 25, 27, 28 and 29 are shown as molecular weight of PEO ($\times 10^6$), percent of PEO, percent nifedipine, percent polyethylene glycol (PEG), and weight of tablet. Thus a tablet indicated to be, "0.9m59,10,30,300 mg" has 59% PEO with a molecular weight of $0.9 \times 10^6$, 10% nifedipine (or 30 mg), 30% PEG, in a 30.0 milligram tablet. The remaining 1% would comprise fillers and lubricants such as magnesium stearate. The compositions of the tablets shown in other Figures are indicated in the description of those Figures.

In the tablets tested in FIGS. 18, 19, 25, 27, 28, and 29, PEG is used as a solubilizing agent to increase the solubility of the low solubility drug nifedipine. Additional solubilizers (as discussed below) are included in the tablets tested in other Figures as indicated. For the purposes of this application for calculating the composition of the excipient and the tablet as a whole, such a solubilizing agent is considered part of the drug, and not part of the excipient. This has been done since the use and proportion of the solubilizing agent is dependent on the particular drug used and the amount thereof. Other solubilizing agents useful in the present invention include cyclodextrins, hydroxypropylcyclodextrins, polyvinylpyrrolidone (PVP) and other solubilizing agents commonly employed in drug compounding.

Sodium lauryl sulfate was added to the dissolution medium to simulate gastrointestinal fluids. The tablet release characteristics were tested in this medium. A sodium lauryl sulfate concentration of 0.27% (9 millimoles) represents the concentration of bile salt in the gastrointestinal tract while the miscellar concentration of bile salt is about 10 millimoles.

Figure 20:
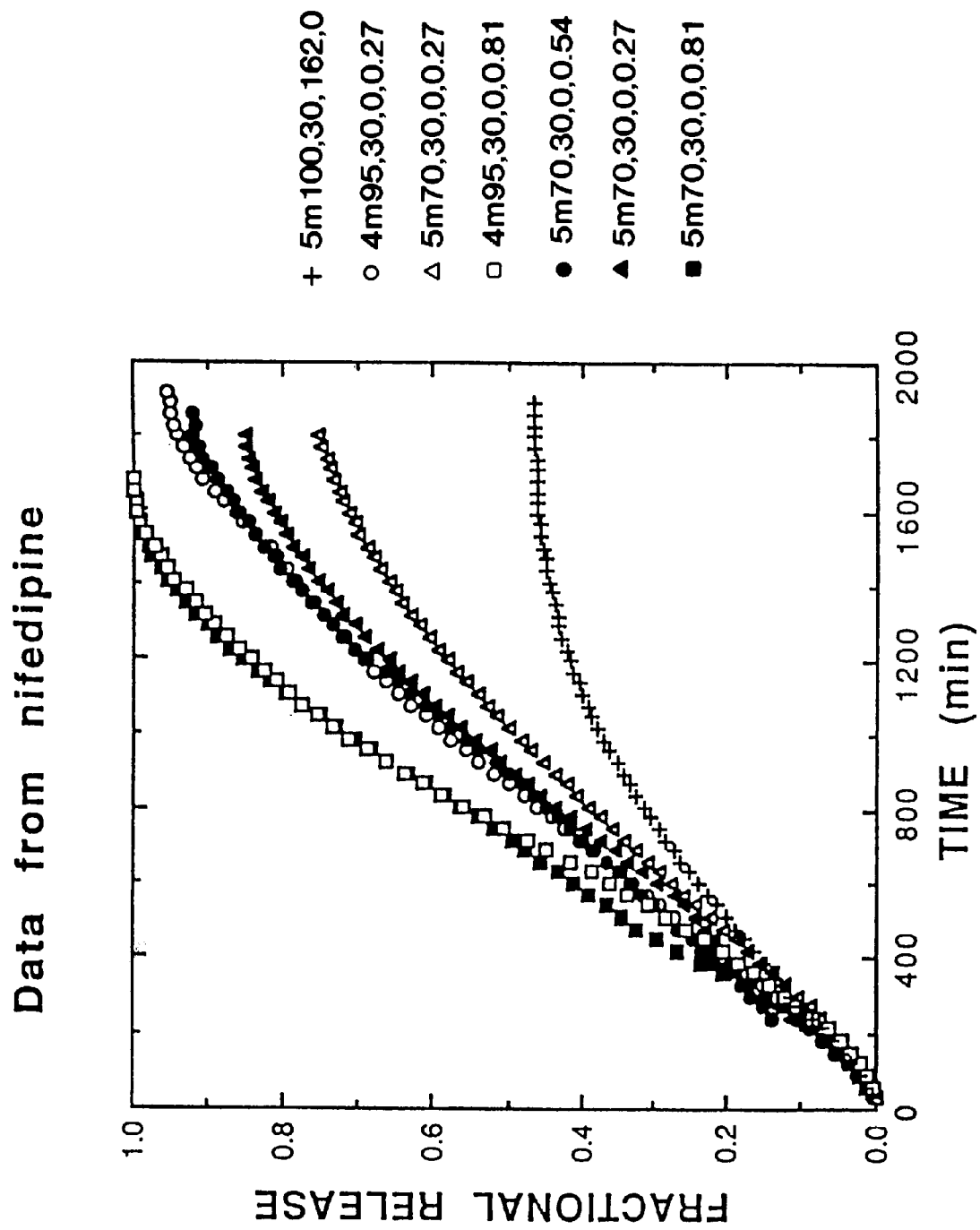
FIG. 20 is a graph of the fractional release of nifedipine from tablets of PEO having varying molecular weights and compositions in various concentrations of dissolution media.

FIG. 20 shows the effects of adding sodium lauryl sulfate (with and without the solubilizer hydroxypropyl-Beta-cyclodextrin (HPβ-CD; 162 mg)) to the dissolution medium on the release kinetics of nifedipine (30 mg) from polyethylene oxide tablets having molecular weights of $4 \times 10^6$ and $5 \times 10^6$. In FIG. 20, the compositions of the tablets tested are shown as molecular weight of PEO($\times 10^6$), milligrams PEO, milligrams nifedipine, milligrams solubilizing agent, and percent sodium lauryl sulfate solution. For example, a tablet indicated to be "5m100, 30, 162, 0" has 100 mg PEO having a molecular weight of $5 \times 10^6$, 30 mg nifedipine, 162 mg solubilizer, and 0 percent sodium lauryl sulfate.

The tablet containing HPO-CD (marked with a "+") in a dissolution medium without sodium lauryl sulfate showed a linear (zero order) release profile in water up to 30% release, followed by leveling off toward an equilibrium concentration at approximately 45–47% release. The remaining nifedipine precipitated as fine particles in the bottom of the dissolution bath. The fine particles likely precipitated in the solution due to the low solubility of nifedipine in water. The other tablets (marked with "○," "△," "□," "●," "▲," and "■") described in FIG. 20 were tested in a dissolution medium including sodium lauryl sulfate at concentrations of 0.27%, 0.54% and 0.81% and showed drug releases of 75%, 85% and 100%, respectively, from polyethylene tablets having a molecular weight of $5 \times 10^6$. The lack of complete dissolution of nifedipine in a dissolution medium containing 0.27% sodium lauryl sulfate solution likely is due to the fact that nifedipine requires a longer period of time to solubilize (approximately 24–30 hrs.), rather than the low solubility of the drug.

FIG. 20 also shows that nifedipine completely dissolves in a 0.81% dissolution medium after being released from PEO tablets having a molecular weight of $5 \times 10^6$. Sodium lauryl sulfate at a concentration of 0.81% is three times as high as the concentration of bile salts in the gastrointestinal tract.

Figure 21:
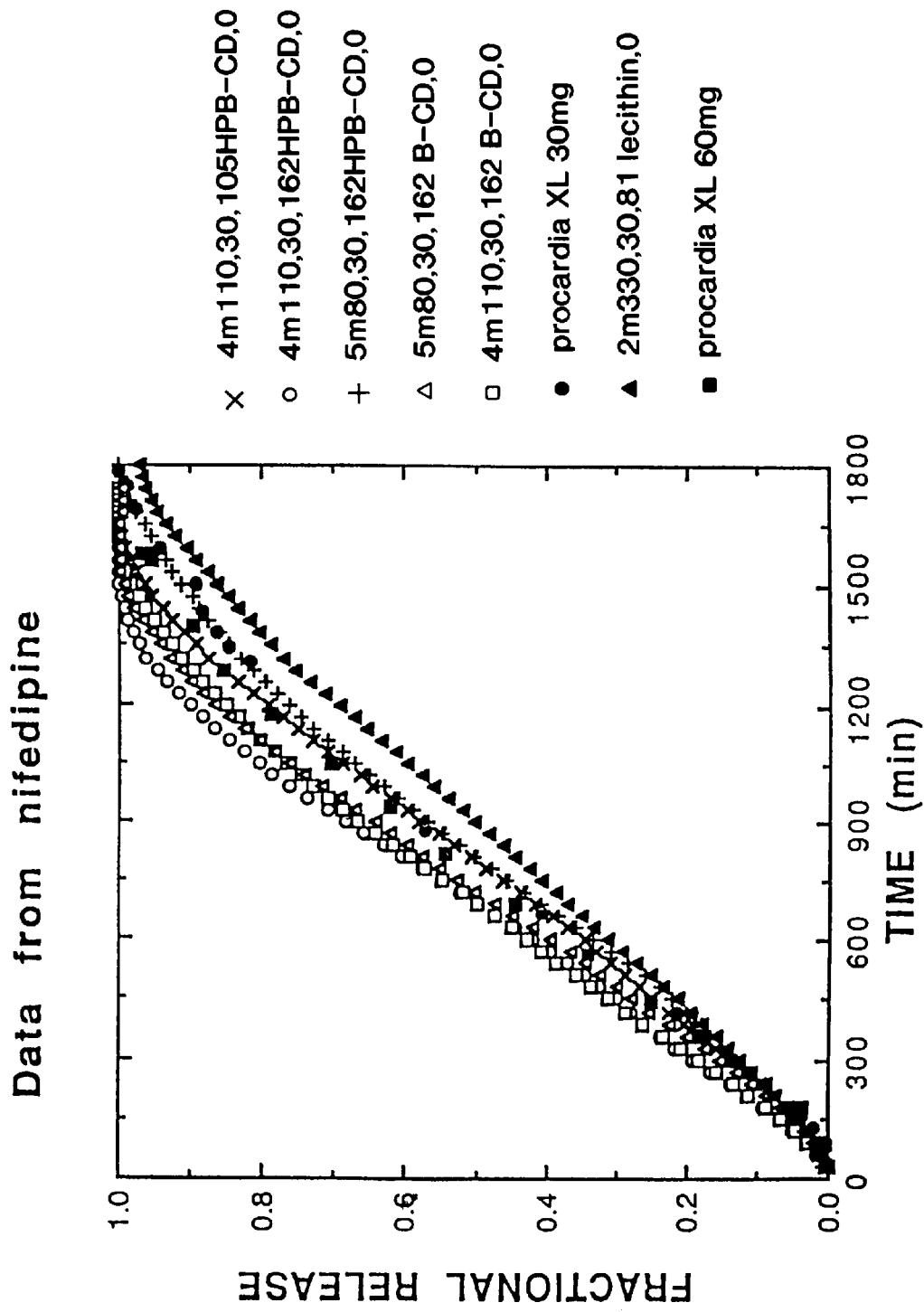
FIG. 21 is a graph of the fractional release of nifedipine from tablets of PEO having varying molecular weights and compositions, compared to the fractional release of nifedipine from Procardia XL™ tablets having 30 or 60 milligrams drug per tablet in the same dissolution medium.

FIG. 21 shows the effect of adding a solubilizing agent such as β-cyclodextrin (β-CD), hydroxylpropyl-β-cyclodextrin (HP β-CD), and lecithin on the release of nifedipine from PEC tablets having molecular weights of $4 \times 10^6$ and $5 \times 10^6$ in a dissolution medium including 0.27% sodium lauryl sulfate. In FIG. 21, the compositions of the tablets tested are shown as molecular weight of PEO($\times 10^6$), milligrams PEO, milligrams nifedipine, milligrams solubilizing agent, and percent sodium lauryl sulfate solution. For example, a tablet indicated to be "5m100, 30, 162, 0" has 100 mg PEO having a molecular weight of $5 \times 10^6$, 30 mg nifedipine, 162 mg solubilizer, and 0 percent sodium lauryl sulfate.

The addition of solublizing agents enhances the dissolution rate of nifedipine from the monolithic polymer matrix as well as dissolution of the nifedipine once it is free from the matrix. Drug release times of approximately 26–30 hours provide ample time for the nifedipine to dissolve in the dissolution medium and also provide sufficient contact between the drug and the solubilizer in the swollen polymer matrix. The release profiles from the PEO tablets followed a sigmoidal pattern indicating that the initial release rate was slow with a lag time of approximately one hour followed by a constant release rate for a period of about 24 hours before tailing off toward complete release. β-CD and HP β-CD are good solubilizers to be incorporated into extended release polymer matrices to enhance the dissolution of water and soluble drugs. They are not yet, however, approved as pharmaceutical excipients. It has been difficult to fabricate lecithin into tablets due to the stickiness and softness of the substance.

Figure 22:
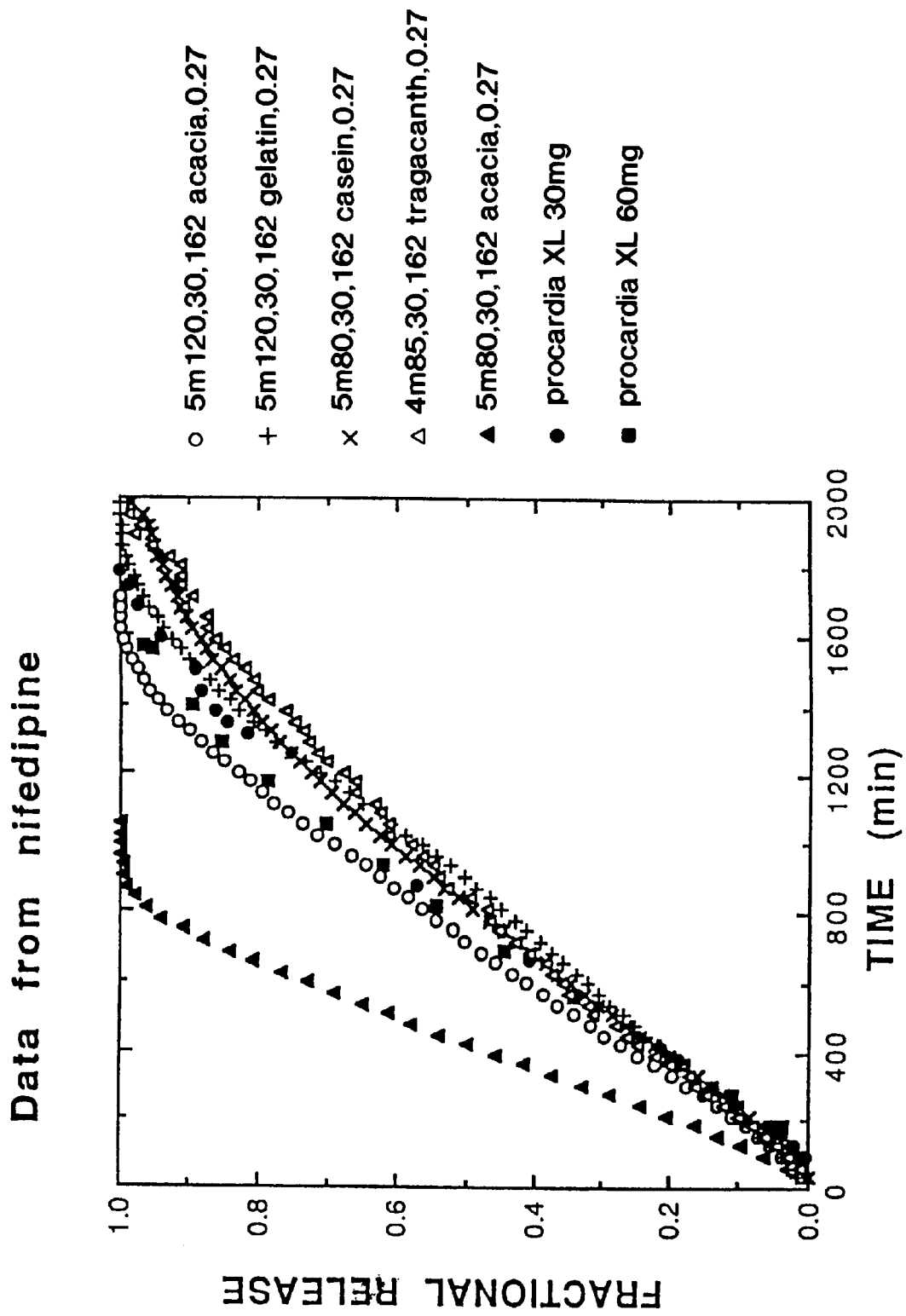
FIG. 22 is a graph of the fractional release of nifedipine from tablets of PEO having varying molecular weights and compositions in a dissolution medium including 0.27% sodium lauryl sulfate, compared to the fractional release of nifedipine from Procardia XL™ tablets having 30 or 60 milligrams drug per tablet.

FIG. 22 shows the effect of naturally occurring polymers such as acacia, gelatin, casein, and tragacanth on the release rates of nifedipine (30 mg) from PEO tablets having molecular weights of $4 \times 10^6$ and $5 \times 10^6$ in a dissolution medium including 0.27 percent sodium lauryl sulfate. The naturally occurring polymers function as emulsifiers and are easy to formulate into tablets. Lecithin may also be used as an emulsifier. In FIG. 22, the compositions of the tablets tested are shown as molecular weights of PEO ($\times 10^6$), milligrams PEO, milligrams nifedipine, milligrams natural polymer, and percent sodium lauryl sulfate. For example, a tablet indicated to be "5 m120, 30, 162 acacia, 0.27" has 120 mg PEO having a molecular weight of $5 \times 10^6$, 30 mg nifedipine, 162 mg acacia, and 0.27% sodium lauryl sulfate.

As FIG. 22 indicates, the release of nifedipine from PEO tablets containing acacia produced similar release profiles to those of PEO tablets containing β-CD, HP β-CD, and lecithin. The release of nifedipine from PEO tablets having a molecular weight of $5 \times 10^6$ including the naturally occurring polymer acacia was twice as fast as the release of nifedipine from PEO tablets having a molecular weight of $5 \times 10^5$ including the cyclodextrins. It was also shown that the period of release of nifedipine from PEO tablets having a molecular weight of $5 \times 10^6$ could be increased to 30 hours by increasing the amount of polymer from 80 milligrams to 120 milligrams per tablet. Acacia is a naturally occurring polysaccharide which has been used to form oil-in-water emulsions with a hydrophilic-lipophilic balance (HLB) value of 8 and may be formed into tablets more easily than synthetic emulsifiers such as sodium oleate and glycerol monostearate. The polymers gelatin, casein and tragacanth have HLB values ranging from 8 to 13.2.

Figure 23:
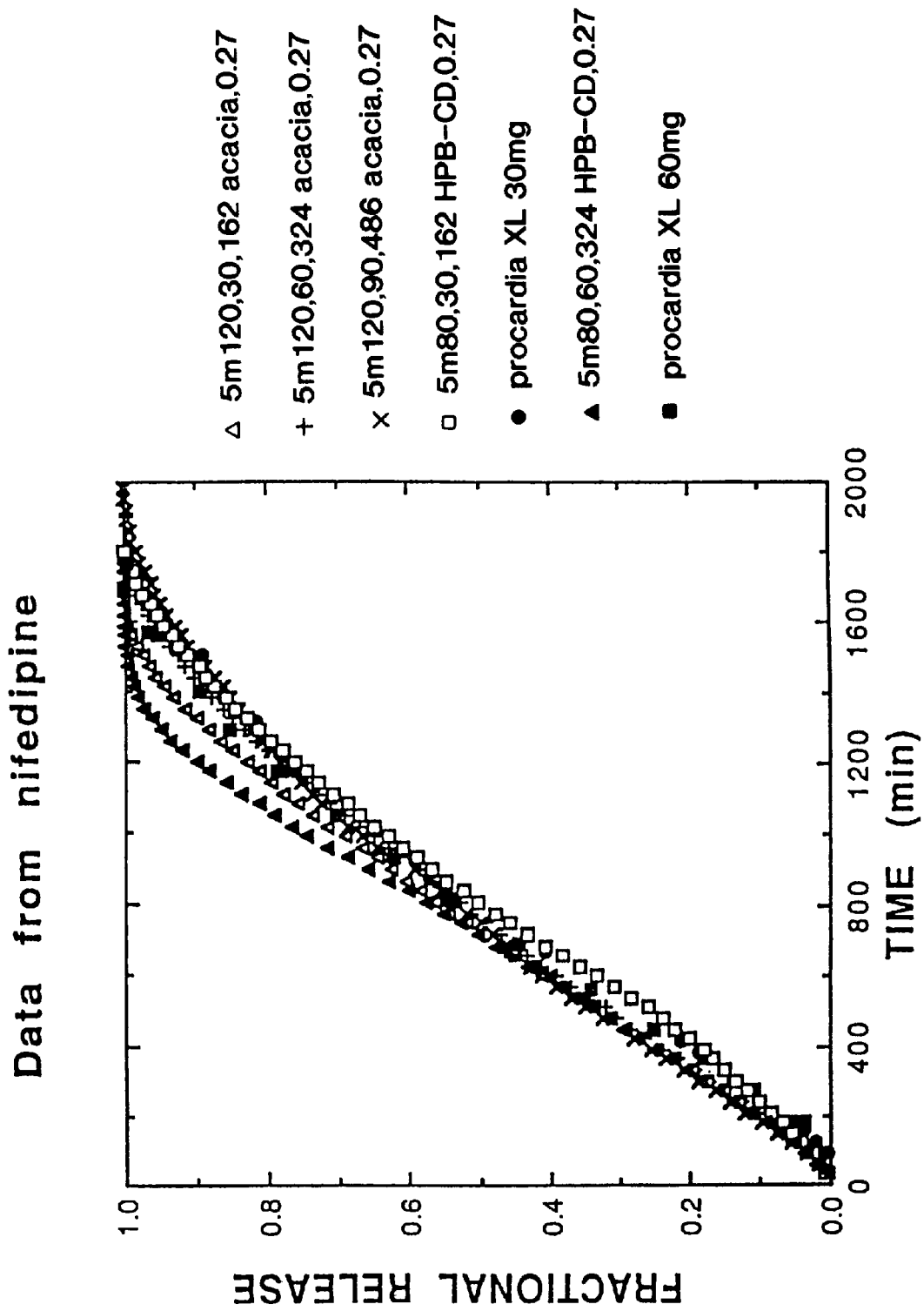
FIG. 23 is a graph of the fractional release of nifedipine from tablets of PEO having a molecular weight of $5 \times 10^6$ and having varying compositions.

FIG. 23 shows that the release of nifedipine from polyethylene oxide tablets having a molecular weight of $5 \times 10^6$ and including varying amounts of polymer, drug, naturally occurring polymer and solubilizer follow release kinetics similar to Procardia XLT (30 mg and 60 mg). In FIG. 23, the compositions of the tablets tested are shown as molecular weight of PEO($\times 10^6$), milligrams PEO, milligrams nifedipine, milligrams natural polymer or solubilizing agent, and percent sodium lauryl sulfate. For example, a tablet indicated to be "5m120, 30, 162 acacia, 0.27" has 120 mg PEO having a molecular weight of $5 \times 10^6$, 30 mg nifedipine, 162 mg acacia, and 0.27% sodium lauryl sulfate. For systems controlled by drug diffusion, similar release kinetics to those of Procardia XL™ (30 mg or 60 mg) can be achieved by substituting for a portion of the active ingredient a water soluble excipient such as lactose. For example, as discussed above with respect to FIG. 6, the release profile of diclofenac sodium from PEO tablets having a molecular weight of $4 \times 10^6$ and containing 39% diclofenac sodium is superimposable (except in the final stage of release) with the release profile of diclofenac sodium from a polyethylene oxide tablet having a molecular weight of $4 \times 10^6$ and containing 20% diclofenac sodium and 19% lactose.

For systems controlled by the erosion of polymer followed by dissolution of the drug from the polymer, it may be necessary to vary the size of the tablet to achieve the desired release kinetics.

Also, for example, for drugs such as nifedipine which require a dissolution enhancing agent, the ratio of nifedipine to the dissolution enhancing agent should be the same in every tablet. The size of the tablet, therefore, should be larger for a 60 milligram nifedipine tablet than for a 30 milligram nifedipine tablet.

Because the ratio of the drug to the dissolution enhancing agent remains the same, the percentage of the dissolution enhancing agent to the total weight of the tablet increases, leading to faster dissolution of the polymer and a shortened total release time of the drug. To compensate for this undesired result, the mass of the PEO in higher dose tablets should be increased so that the ratio of the dissolution enhancing agent to the mass of the polymer remains constant. FIG. 23 shows that the in vitro release profiles of Procardia XL™ (30 milligrams and 60 milligrams) and, the release profiles of the tablets prepared according to this invention are superimposable on one another with a minor adjustment for formulation compositions. That is, a minor adjustment for the amount of polymer and the ratio of the drug enhancing agent to the drug.

Figure 24:
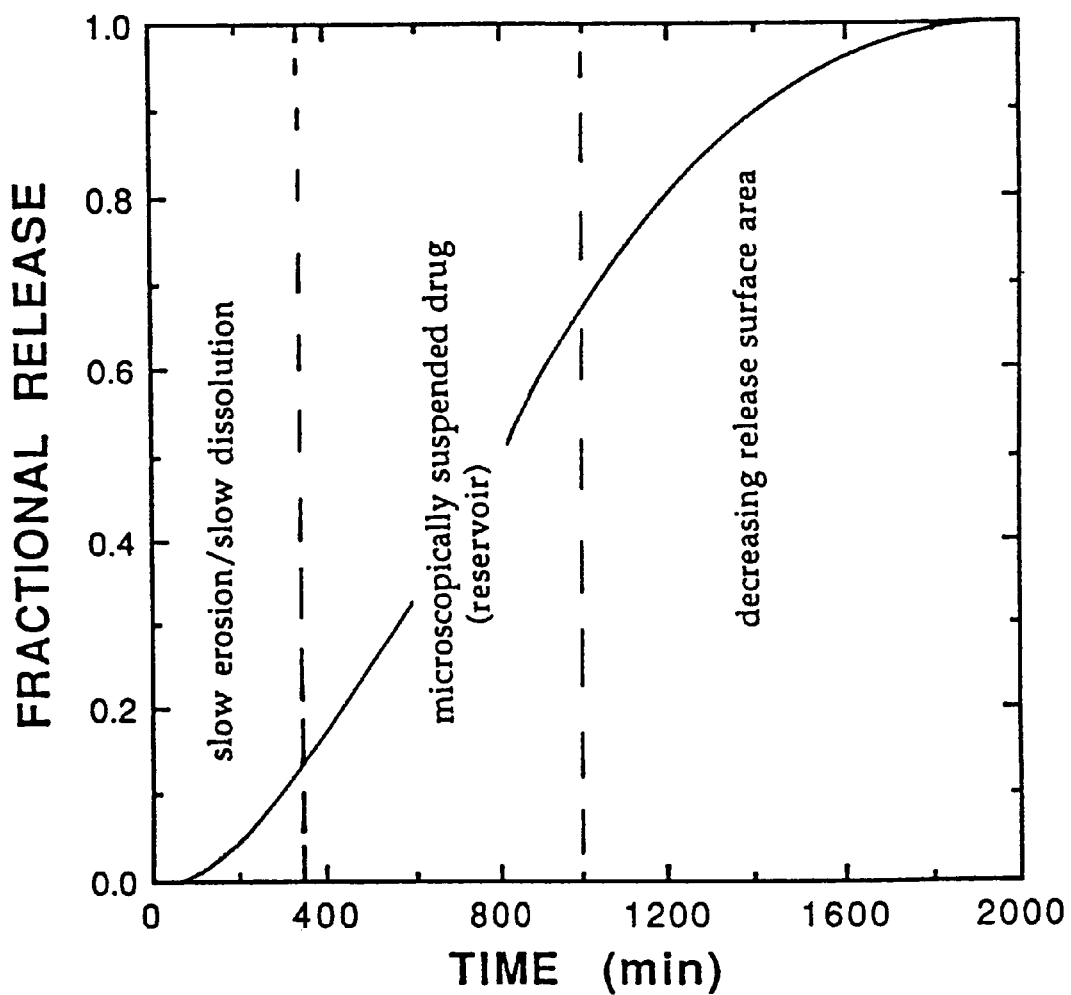
FIG. 24 is a graph of the release of nifedipine from PEO tablets showing the different phases of drug release.

FIG. 24 shows that release of nifedipine from PEO tablets follows sigmoidal pattern. An initial time lag is shown during which time the slow erosion and slow dissolution of the polymer and drug, respectively, takes place. This is followed by constant drug release from about 15% to about 70% where the nifedipine is microscopically suspended in the dissolution medium. Then, there is a decreasing drug release phase followed by complete tailing off of the drug release at the end of drug release.

FIGS. 21, 22, 23 and 24 show that the drug release profiles of nifedipine from PEO tablets appear initially to be delayed for a period of approximately one hour. This is followed by an extended linear release (15 to 70% of total release) before tailing toward complete release. Because nifedipine is a drug of low solubility, drug diffusion does not contribute significantly to the overall drug release mechanism. Instead, the erosion of the swollen polymer controls the release kinetics of nifedipine from polyethylene oxide tablets. The sigmoidal release profile of nifedipine from PEO tablets does not follow the conventional theory that the release of water insoluble drugs is dependent on the rate of erosion of the polymer. PEO tablets having molecular weights greater than $4\times10^6$, however, provide high swelling and low erosion in the early stage of drug release. The slow erosion rate of the polymer causes the drug to be released slowly and to dissolve slowly in the dissolution medium. This pattern explains the initial time lag and slowly increasing release rate up to 15% of drug release. The drug release rate is constant then from 15% to 70% release. As the drug is released from the PEO tablets, it is microscopically suspended as indicated by the fact that the dissolution of released drug lasts for approximately three hours after the polymer completely dissolves in the dissolution medium.

The suspended drug acts as a reservoir and the release rate of the drug from the PEO tablets is balanced with the dissolution rate of the suspended drug resulting in constant release kinetics. In contrast, for extended release dosage forms of highly water soluble drugs, the drug release is coincidental with the disappearance of the swollen polymer. That is, as the swollen polymer is dissolved, the drug is simultaneously released and dissolved in the dissolution medium. If the dissolution medium does not solubilize the released drug during this period, the excess amount of the drug will become suspended and precipitate as discussed above with respect to FIG. 20. Incorporating a solubilizing agent into the PEO tablets will aid in releasing low solubility drugs from the tablets. As the period of release increases the amount of the suspended drug will decrease causing the release profile to gradually tail off towards complete release.

Figure 25:
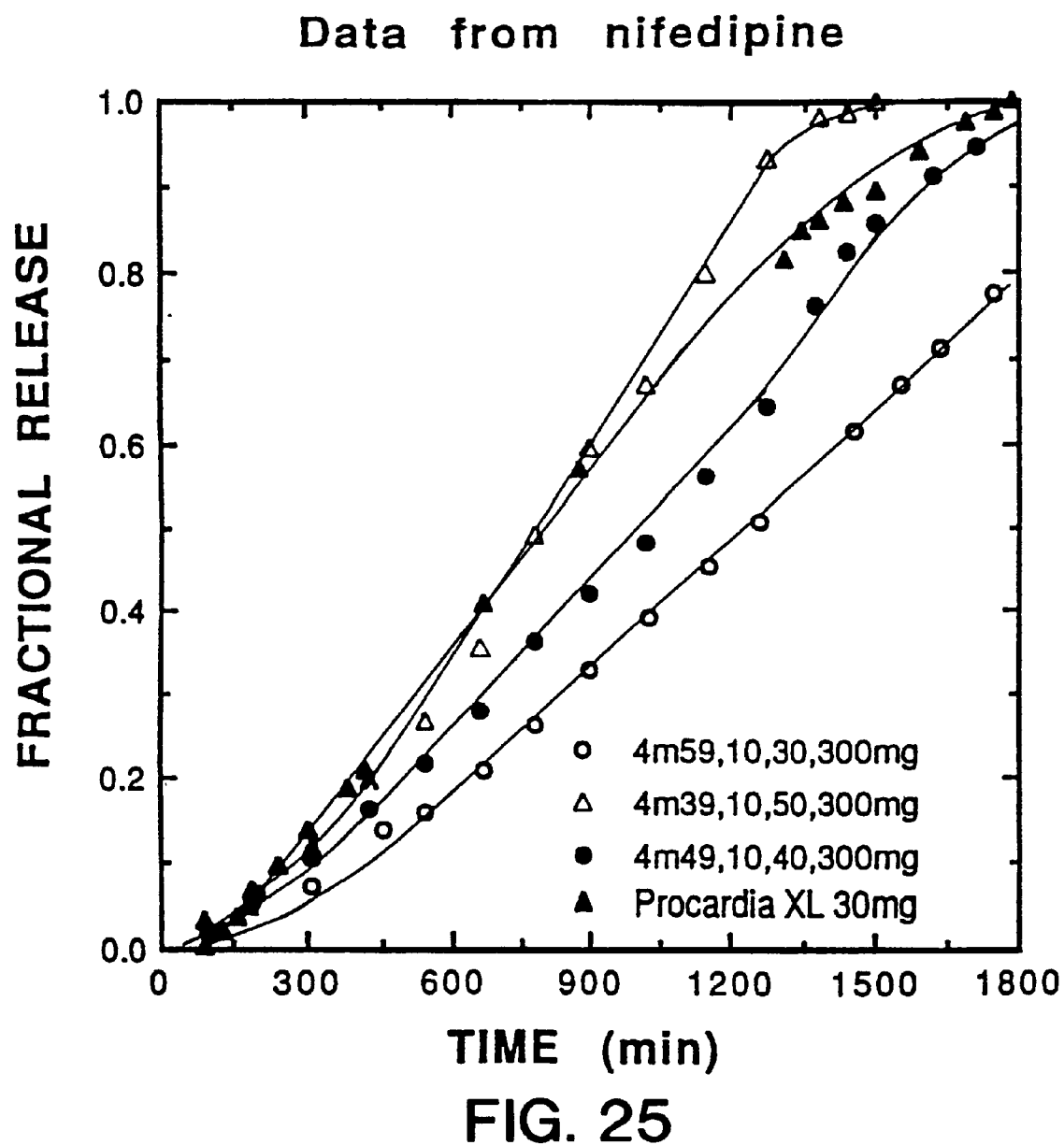
FIG. 25 is a graph of the fractional release of nifedipine from tablets of PEO having a molecular weight of $4.0 \times 10^6$ and having various amounts of polyethylene glycol added thereto, compared to the fractional release of nifedipine from a Procardia XL™ tablets having 30 mg drug per tablet.
Figure 28:
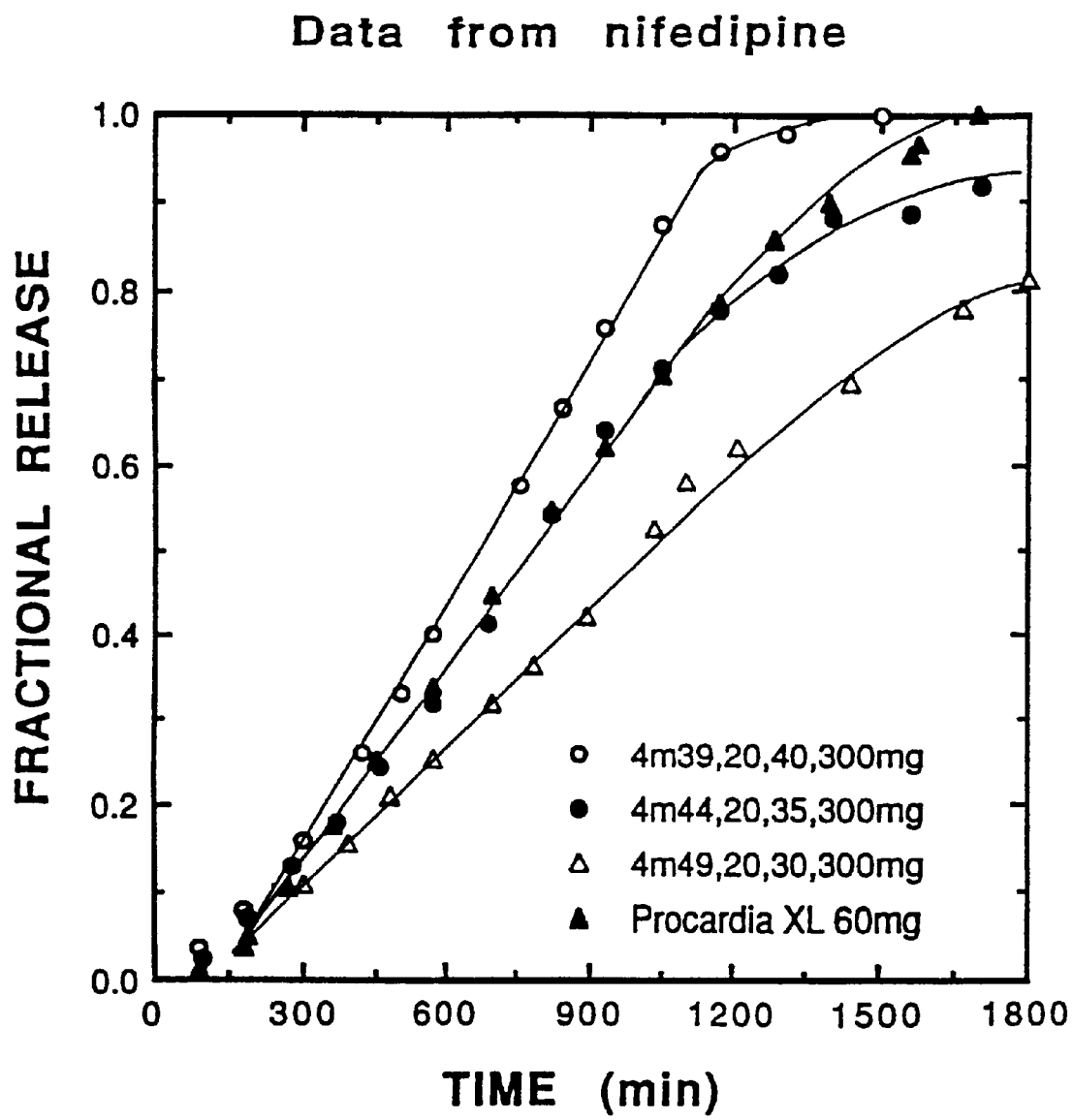
FIG. 28 is a graph of the fractional release of nifedipine from tablets of PEO having a molecular weight of $4.0 \times 10^6$ and having various amounts of polyethylene glycol added thereto, compared to the fractional release of nifedipine from a Procardia XL™ tablets having 60 mg drug per tablet.
Figure 29:
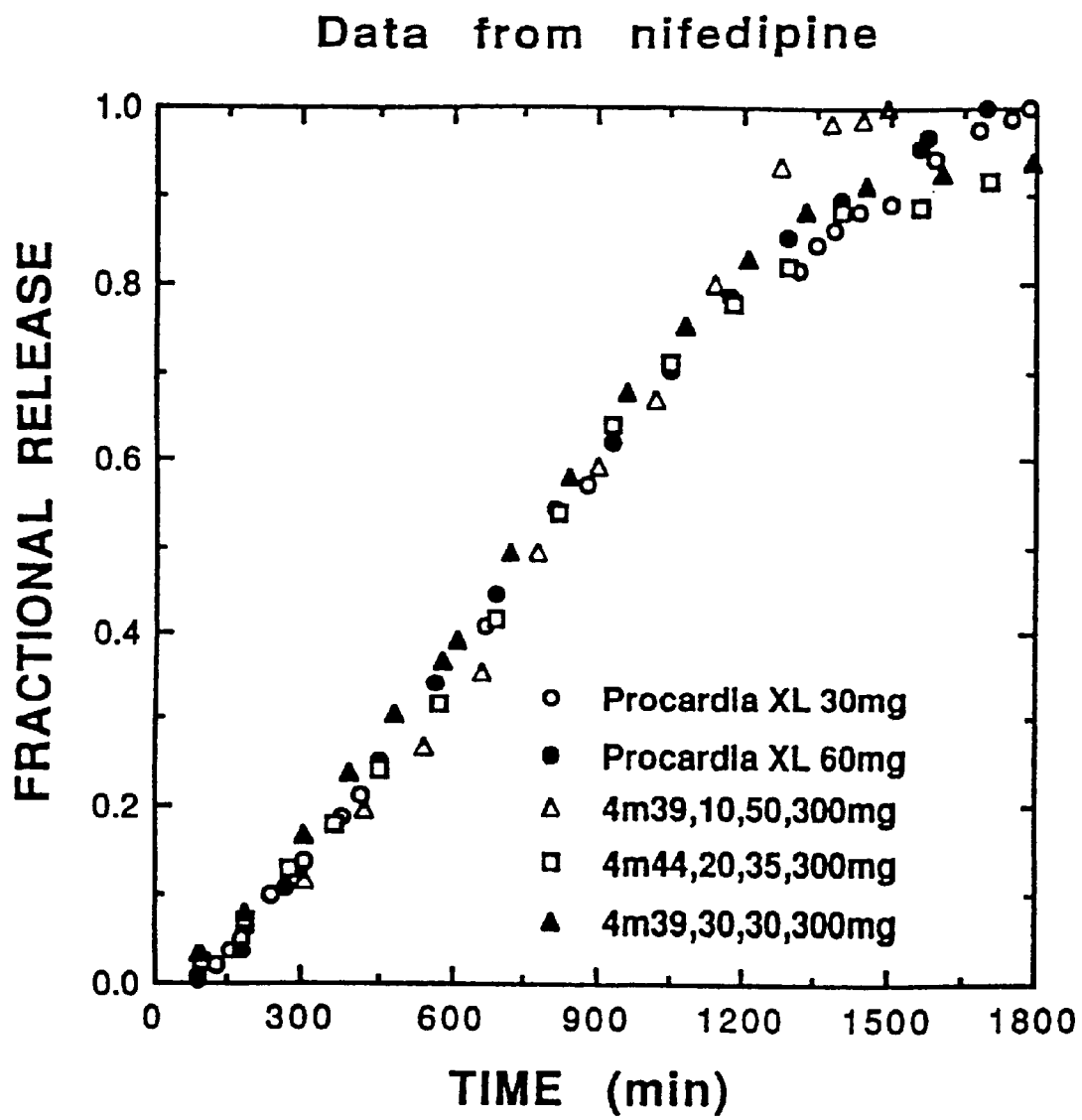
FIG. 29 is a graph of the fractional release from Procardia XL™ tablets having 30 mg and 60 mg of drug per tablet compared to the fractional release of nifedipine from tablets of PEO having a molecular weight of $4.0 \times 10^6$ and having various amounts of nifedipine therein.

FIG. 25 shows that a 300 mg PEO tablet having 40 to 50% PEG and 30 mg nifedipine performs very similarly to a 30 mg Procardia XL™ tablet. FIG. 28 shows that a 300 mg PEO tablet having about 350 PEG and 60 mg nifedipine performs very similarly to a 60 mg Procardia XL™ tablet.

Figure 26:
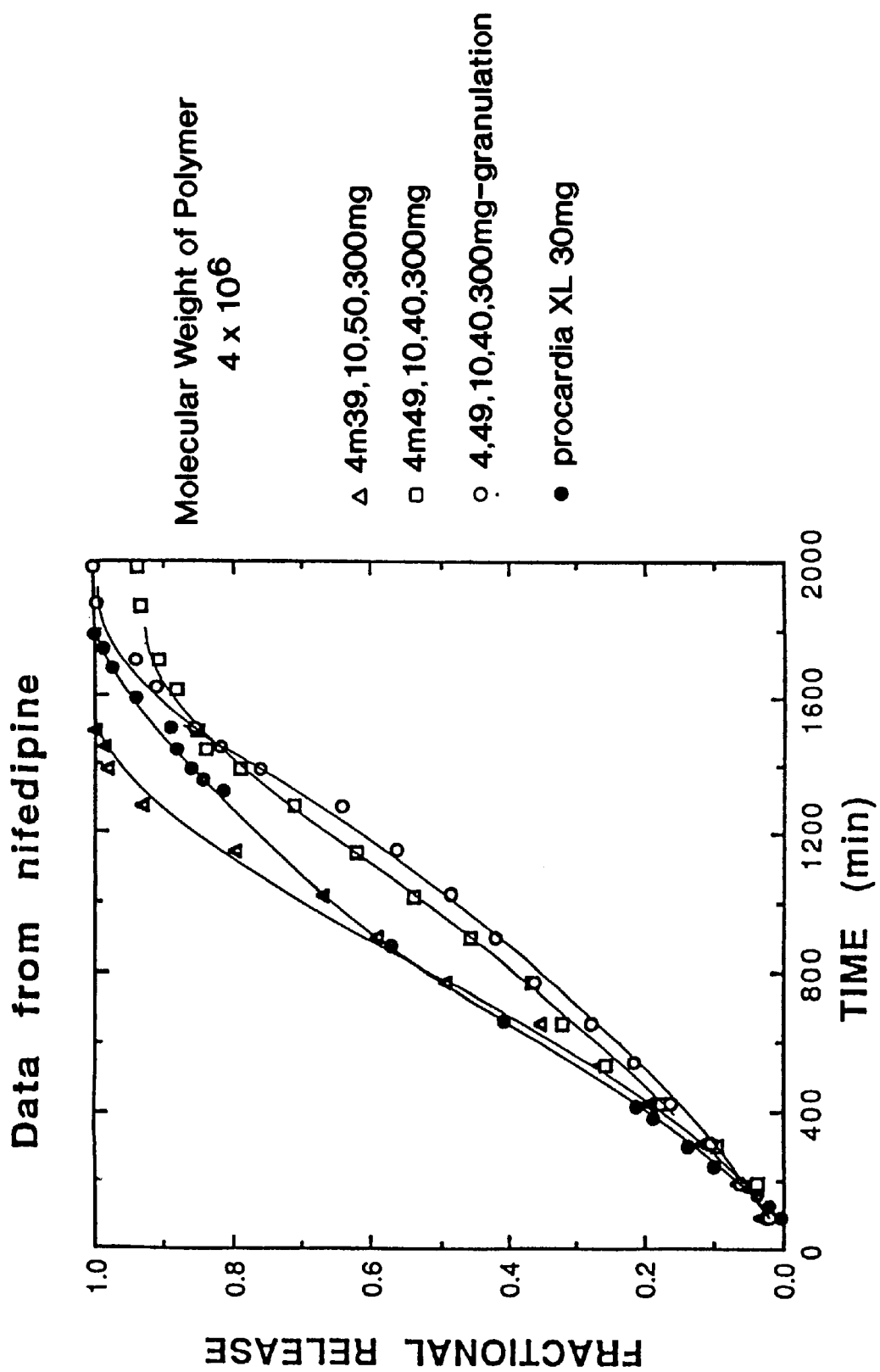
FIG. 26 is a graph of the fractional release of nifedipine or granulated nifedipine from tablets of PEO having a molecular weight of $4 \times 10^6$, 10% nifedipine, and various amounts of PEG, compared to the fractional release of nifedipine from a Procardia XL™ tablet having 30 mg drug per tablet.
Figure 27:
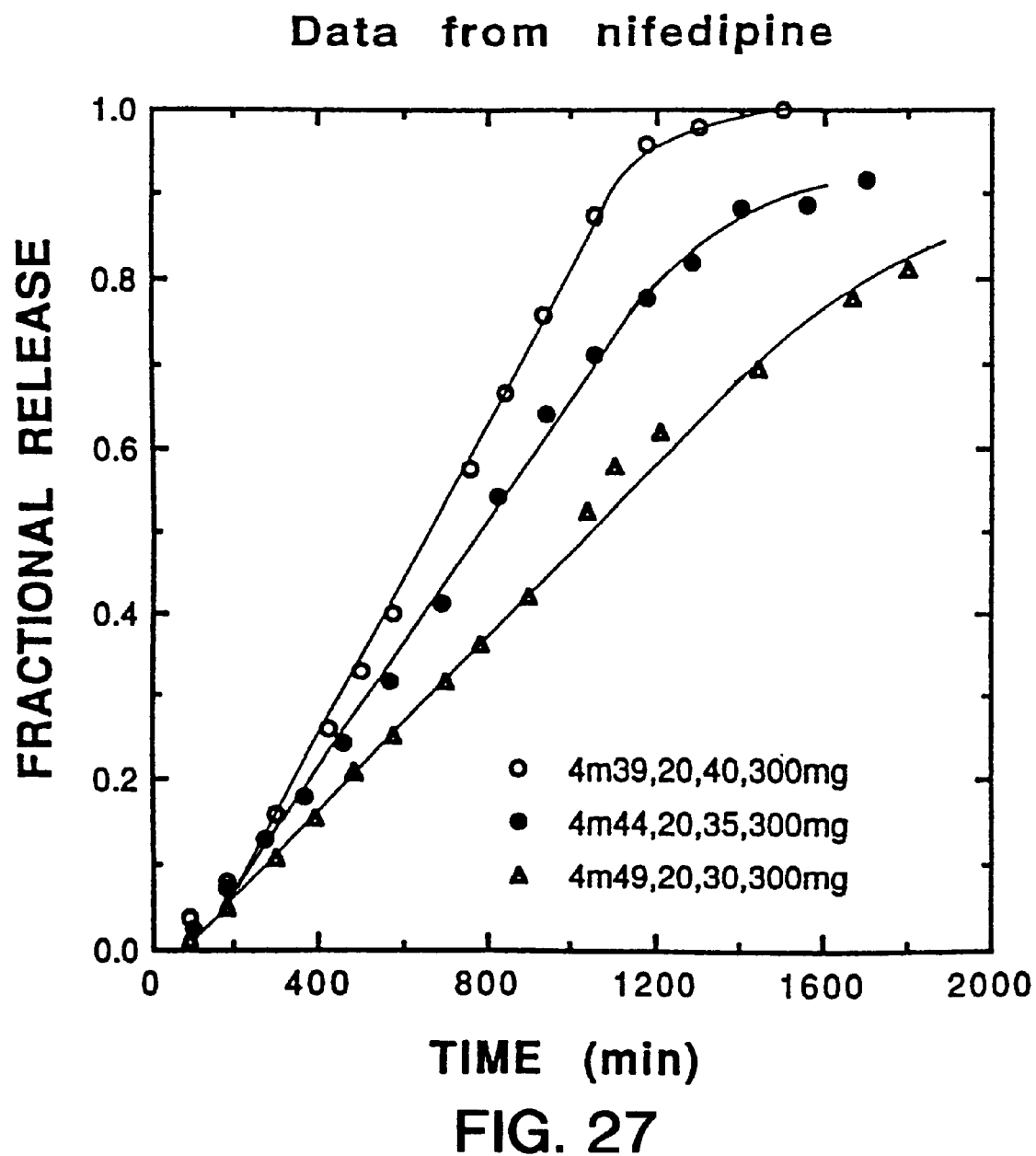
FIG. 27 is a graph of the fractional release of nifedipine from tablets of PEO having a molecular weight of $4.0 \times 10^6$ having 20 percent nifedipine and having various amounts of polyethylene glycol added thereto.

FIG. 26 shows that nifedipine or granulated nifedipine released from PEO tablets having a molecular weight of $4\times10^6$ and 10% drug loading performed similarly to a 30 mg Procardia XL™ tablet. The nifedipine tablets were 9.5 mm in diameter and weighed 300 mg, and were compressed to 2000 pounds per square inch. In FIG. 26, the compositions of the tablets tested are shown as molecular weight of PEO ($\times10^6$), percent of PEO, percent nifedipine, percent polyethylene glycol (PEG), and weight of tablet. Thus, a tablet indicated to be "4 m 39, 10, 50, 300 mg" has 39% PEO having a molecular weight of $4\times10^6$, 10% nifedipine (or 30 mg), 50% PEG, in a 300 milligram tablet. The remaining 1% comprises fillers and lubricants. The granulated nifedipine formulation was tested in a dissolution medium which did not include sodium lauryl sulfate. The other tablets presented in FIG. 26 were tested, however, in a dissolution medium including 0.54% sodium lauryl sulfate.

The release of nifidipine from the PEO tablets was zero order up to 80% to 90% release. The solubilizer PEG was included in the tablets to enhance dissolution of the nifedipine. However, a lag time was observed. The lag time is attributed to the time required for the edge of the polymer matrix to hydrate before dissolution of the drug. Because of the low solubility of nifedipine, the particle size of nifedipine within the polymer matrix is important. Nifedipine, therefore, in one trial was granulated, dissolved in ethanol, and dried in a dark room. The granulated nifedipine was then mixed with the PEO. The release kinetics of the granulated nifedipine were similar to the release kinetics of Procardia XL™ indicating that the granulated nifedipine facilitates dissolution of the nifedipine in water. The increased dissolution likely resulted from the finer nifedipine particles.

The ungranulated nifidipine tablets and the Procardia XL™ tablets were tested in dissolution mediums with sodium lauryl sulfate while the granulated nifedipine tablet was tested in a dissolution medium without sodium lauryl sulfate.

Figure 30:
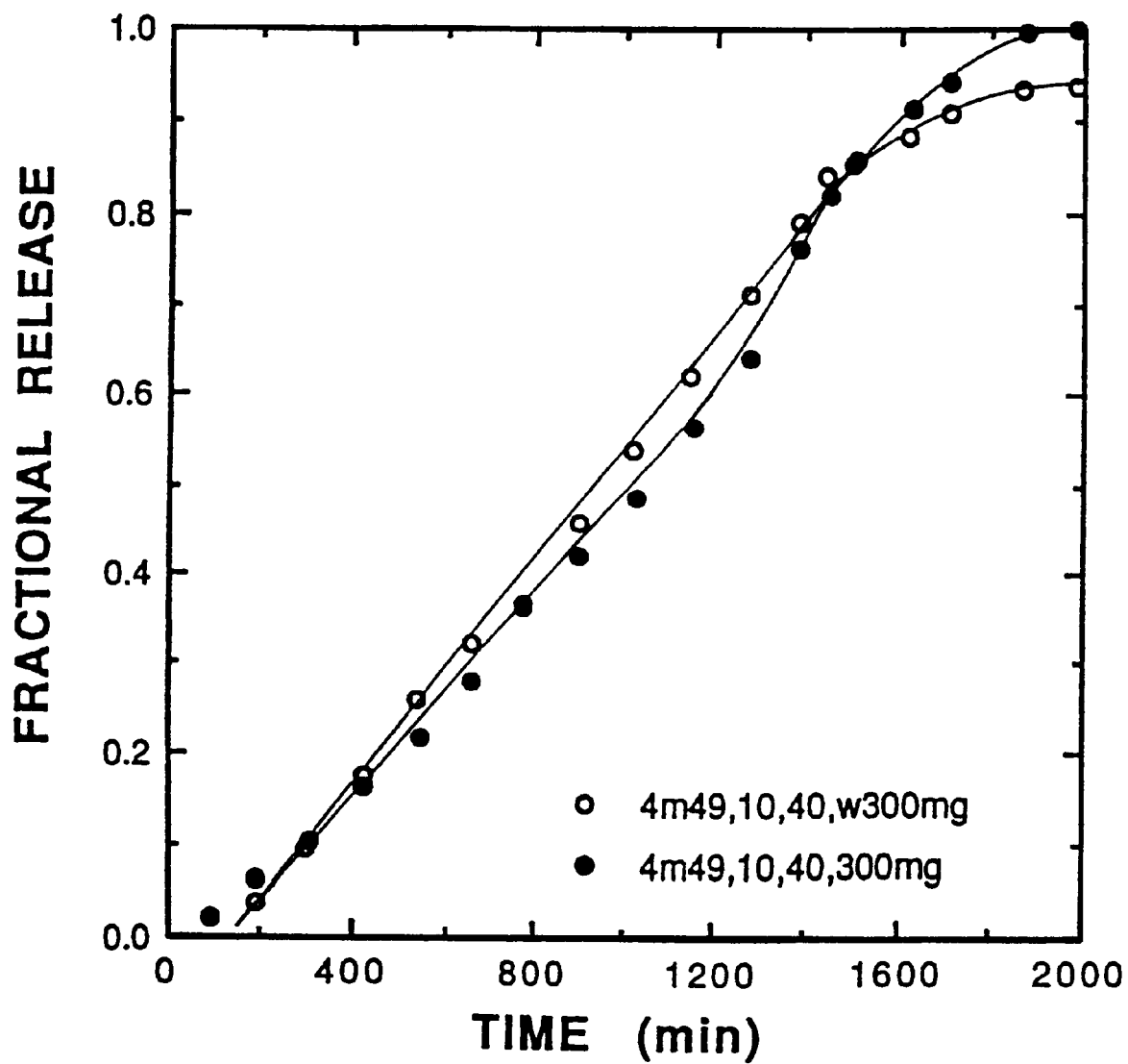
FIG. 30 is a graph of the fractional release of nifedipine from tablets of PEO having a molecular weight of $4.0 \times 10^6$ and 10 percent nifedipine per tablet.

FIG. 30 shows the fractional release of nifedipine from tablets of PEO having a molecular weight of $4\times10^6$. The tablets (300 mg tablets) were tested both in water and 0.54% sodium lauryl sulfate. The tablets were found to perform well.

Figure 31:
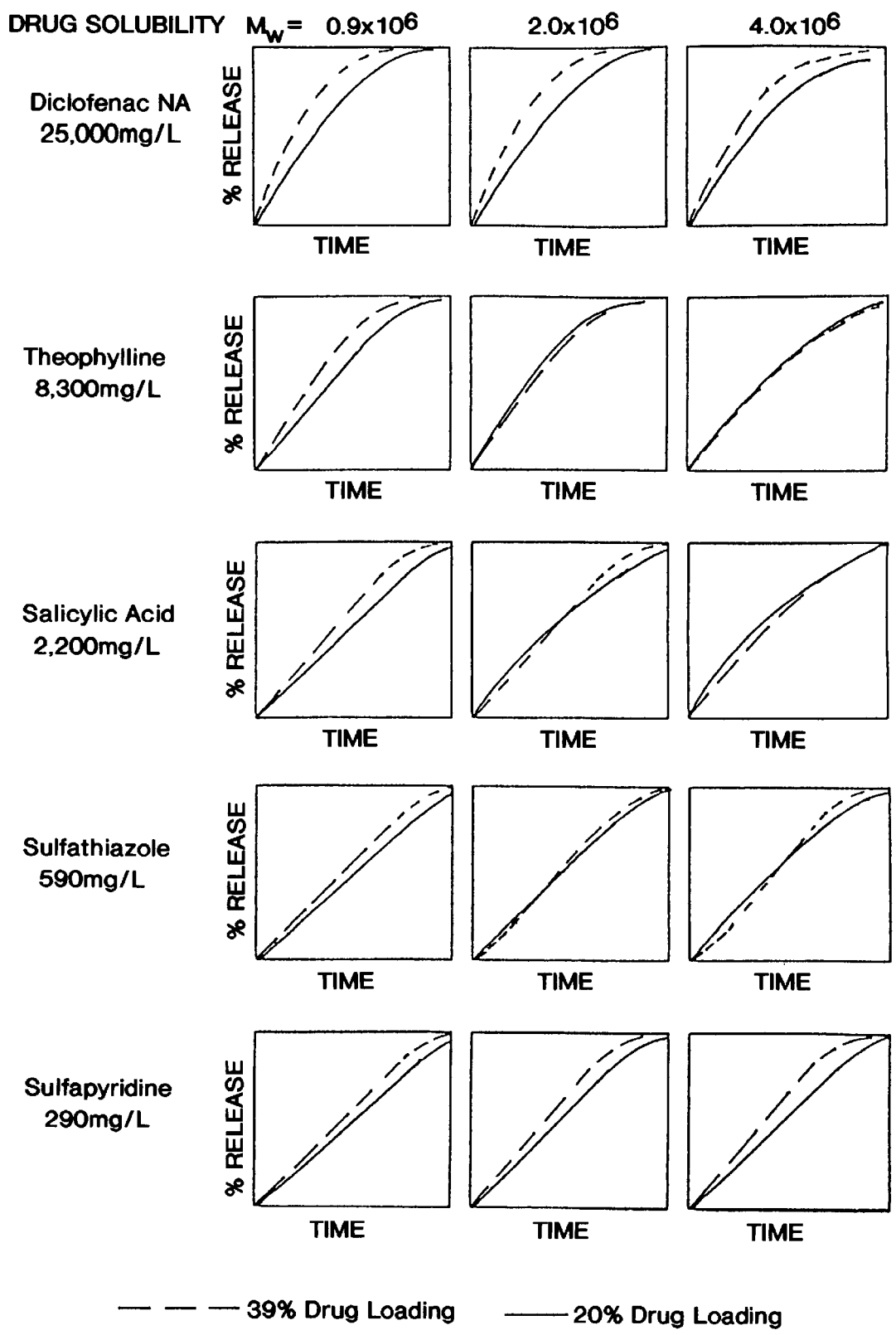
FIG. 31 shows several graphs of the fractional release of various drugs having different solubilities, and various drug loadings from PEO tablets having molecular weights of $0.9 \times 10^6$, $2 \times 10^6$ and $4 \times 10^6$.

FIG. 31 shows the effects of drug loading, drug solubility and polymer molecular weight on release kinetics. A set of tablet punches with flat surfaces were used to prepare the tablets having diameters of 11.1 mm and weights of 550 mg except for the sulfathiazole tablets, which were 9.5 mm in diameter and weighed 400 mg. All the tablets were compressed to 4000 pounds per square inch. For sulfathiazole (solubility 590 mg/l), the release profiles from 20% and 39% loaded PEO polymer having a molecular weight of $4\times10^6$ cross each other at about 50% release. The diffusion of the dissolved drug in the 20% loaded tablets is more rapid at the early stage of release than the diffusion at that stage for the 39% loaded tablets. For salicylic acid (solubility 2200 mg/l), the release profiles from 20% and 39% loaded PEO tablets having a molecular weight of $2\times10^6$ cross each other at about 50% release.

For sulfapyridine (solubility 290 mg/l), however, the release profiles from 39% loaded PEO tablets were shifted to the left of the release profiles from 20% loaded tablets. This indicates that the drug is released in a shorter period of time. The shorter release time is attributable to the fact that drug release for very low solubility drugs is controlled by erosion of the polymer followed by dissolution of the drug from the eroded polymer. Also, for tablets formed with PEO having a molecular weight of $0.9\times10^6$, the release profiles of the 39% drug loaded tablets were similarly shifted indicating that drug release is controlled by the swelling/erosion process of the polymer. This gives rise to faster dissolution of the polymer with zero order release kinetics. The release kinetics for the high solubility drugs such as diclofenac sodium from PEO tablets having a molecular weight of $0.9\times10^6$ and 20% drug loading exhibited linear drug release with n equal to 0.93. This indicates that drug diffusion is the controlling factor for the release kinetics.

It is understood that various other modifications will be apparent to one skilled in the art without departing from the spirit and scope of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed:

1. A controlled release tablet consisting essentially of a single homogeneous mixture of a pharmaceutical agent selected from the group consisting of nifedipine, diclofenac sodium, salicylic acid, theophylline anhydrous, sulfapyridine, sulfadrazine, propranolol hydrochloride, diltiazem hydrochloride, glipizide, and sulfathiazole, a solubilizing agent, and an excipient, wherein said excipient comprises:

polyethylene oxide and a lubricant; and wherein the pharmaceutical agent is released from the tablet at a rate expressed as $M_t/M_T = kt^n$ where:

t is time, $M_t$ is the amount of the pharmaceutical agent which has been released at time t, $M_T$ is the total amount of the pharmaceutical agent contained in the tablet, k is a constant, and n is the release kinetics exponent; and wherein the molecular weight and the solubility, respectively, of said polyethylene oxide and the pharmaceutical agent are selected such that n is about 0.89 to 1.0.

2. A controlled release tablet according to claim 1 wherein said polyethylene oxide has an average molecular weight in the range of about 900,000 to 5,000,000.

3. A controlled release tablet according to claim 1 wherein said lubricant is magnesium stearate.

4. A controlled release tablet according to claim 3 wherein said lubricant is present in an amount up to 3% by weight of said tablet.

5. A controlled release tablet according to claim 1 wherein said excipient further comprises a diluent.

6. A controlled release tablet according to claim 5 wherein said diluent is selected from the group consisting of lactose, dextrose, sucrose, and calcium phosphate.

7. A controlled release tablet according to claim 6 wherein said diluent is present in an amount of up to 50% by weight of said excipient.

8. A controlled release tablet according to claim 1 wherein said pharmaceutical agent is nifedipine.

9. A controlled release tablet according to claim 1 wherein said pharmaceutical agent is present in an amount of from about 10% to about 40% by weight of said tablet, including said excipient.

10. A controlled release tablet consisting essentially of a single homogenous mixture of a pharmaceutical agent and an excipient, wherein said excipient comprises:

19 to 43% by weight polyethylene oxide;

up to 3% by weight magnesium stearate; and 55 to 80% by weight acacia; and wherein said pharmaceutical agent is nifedipine and is present in an amount of from 9 to 13% by weight of said tablet.

11. A controlled release tablet consisting essentially of a single homogeneous mixture of a pharmaceutical agent nifedipine, a solubilizing agent, and an excipient, wherein said excipient comprises:

polyethylene oxide and a lubricant; and the swelling rate of said polyethylene oxide is equal to the dissolution rate of said polyethylene oxide when the polyethylene oxide is swollen.

12. The controlled release tablet of claim 11 wherein the excipient comprises at least 50% polyethylene oxide and a lubricant.

13. The controlled release tablet of claim 11 wherein said tablet has an aperture therethrough.

14. The controlled release tablet of claim 11 wherein the solubilizing agent is selected from the group consisting of polyethylene glycol, cyclodextrins, hydroxypropylcyclodextrins, lecithin, polyvinylpyrrolidone (PVP), acacia, lecithin gelatin, casein, and tragacanth.

15. The controlled release tablet of claim 11 wherein the polyethylene oxide has an average molecular weight in the range of about 900,000 to 5,000,000.

16. The controlled release tablet of claim 11 wherein said lubricant is magnesium stearate.

17. The controlled release tablet of claim 11 wherein said lubricant is present in an amount up to 3% by weight of said excipient.

18. The controlled release tablet of claim 11 wherein said excipient further comprises a diluent.

19. The controlled release tablet of claim 11 wherein said diluent is selected from the group consisting of lactose, dextrose, sucrose, and calcium phosphate.

20. The controlled release tablet of claim 11 wherein said diluent is present in an amount of up to 50% by weight of said excipient.

21. The controlled release tablet of claim 11 wherein said nifedipine is present in an amount of from about 10% to about 40% by weight of said tablet.

22. A controlled release pharmaceutical tablet consisting essentially of a single homogeneous mixture of the pharmaceutical agent nifidipine, a solubilizing agent selected from the group consisting of polyethylene glycol, acacia, lecithin gelatin, casein, and tragacanth, and an excipient, wherein said excipient comprises polyethylene oxide and a lubricant and at least 50 percent by weight of said excipient is polyethylene oxide having a molecular weight of from 900,000 to 5,000,000.

23. The controlled release tablet of claim 22 in which the solubilizing agent is selected from the group consisting of acacia, gelatin, casein and tragacanth.

24. The controlled release tablet of claim 22 in which the solubilizing agent is acacia.

25. The controlled release tablet of claim 22, 23, or 24 in which the tablet exhibits zero order release kinetics for the nifidipine when the tablet is swollen in the presence of aqueous media.

* * * * *